(12) United States Patent
Brook et al.

(10) Patent No.: US 6,170,746 B1
(45) Date of Patent: Jan. 9, 2001

(54) SYSTEM AND METHOD FOR TRACKING DRUGS IN A HOSPITAL

(75) Inventors: Douglas J. Brook; Mark S. Morrow, both of Dayton; Raymond D. Tavener, Lebanon, all of OH (US)

(73) Assignee: Monarch Marking Systems, Inc., Dayton, OH (US)

( * ) Notice: Under 35 U.S.C. 154(b), the term of this patent shall be extended for 0 days.

(21) Appl. No.: 09/133,762

(22) Filed: Aug. 12, 1998

(51) Int. Cl.[7] .................................................. G06F 17/60
(52) U.S. Cl. ....................................... 235/385; 235/462.01
(58) Field of Search ..................................... 235/380, 382, 235/383, 385, 375, 462.15, 462.01, 462.45; 705/2, 3, 22, 28

(56) References Cited

U.S. PATENT DOCUMENTS

| | | | | |
|---|---|---|---|---|
| 4,850,009 | * | 7/1989 | Zook et al. | 235/375 |
| 4,857,716 | * | 8/1989 | Gombrich et al. | 235/375 |
| 4,916,441 | * | 4/1990 | Gombrich | 235/380 |
| 5,371,348 | * | 12/1994 | Kumar et al. | 235/472 |
| 5,597,995 | * | 1/1997 | Williams et al. | 235/375 |
| 5,602,377 | * | 2/1997 | Beller et al. | 235/462.15 |
| 5,700,998 | * | 12/1997 | Palti | 235/375 |
| 5,762,235 | * | 6/1998 | Coughlin | 221/6 |
| 5,845,264 | * | 12/1998 | Nelhaus | 235/375 |
| 6,021,392 | * | 2/2000 | Lester et al. | 705/2 |

* cited by examiner

Primary Examiner—Thien M. Le
Assistant Examiner—Larry D. Taylor
(74) Attorney, Agent, or Firm—McAndrews, Held & Malloy, Ltd.

(57) ABSTRACT

A drug tracking system and method for use in hospitals, pharmacies, etc. uses a portable barcode scanning and printing system to reduce errors in the tracking information and to facilitate the ease and efficiency of the drug tracking operation. The portable scanning and printing system automatically prompts the user to enter data necessary for tracking one or more drugs. The portable scanning and printing system also prompts the user to select a particular drug and/or quantity. Automatic verification of the user entered data is performed by the portable system so as to warn the user via a displayed message that the wrong drug and/or quantity was selected or to prompt the user to recount and/or re-enter data so that any discrepancies can be immediately corrected. The portable scanning and printing system also prints alpha-numeric and barcode information on labels that are used to continue the drug tracking operation at other locations. Because the portable scanning and printing system is mobile, all of the drug tracking operations can be performed at the drug's situs to improve the accuracy of the drug tracking operation.

43 Claims, 27 Drawing Sheets

SYSTEM AND METHOD FOR TRACKING DRUGS IN A HOSPITAL

TECHNICAL FIELD

The present invention relates to a drug tracking system and method for use in hospitals, pharmacies, etc. for tracking drugs including narcotics; and more particularly to such a system and method using a portable barcode scanning and printing system to reduce errors in the tracking information, to facilitate the ease and efficiency of tracking and to ensure reproducibility and security.

CROSS-REFERENCE TO RELATED APPLICATIONS

N/A

STATEMENT REGARDING FEDERALLY SPONSORED RESEARCH OR DEVELOPMENT

N/A

BACKGROUND OF THE INVENTION

Known methods for tracking drugs, particularly narcotics, in hospitals or the like have been manual. The narcotics are typically located in a narcotics safe. The removal of drugs from the drug safe for distribution to nursing stations while tracking the removal is a very time intensive procedure prone to inaccuracies, as is the tracking of the addition of drugs to the narcotics safe. Typical manual tracking procedures are as follows.

In order to distribute the drugs from the safe to the nursing stations, a "pick-list" is first manually generated. A hospital technician gathers drug disposition records and 24 hour nursing audit records from each nursing station. Based upon these records, the technician determines the quantity of each drug at a nursing station and then determines whether that quantity of the drug is below a par level for that particular nursing station. If the final count of a drug is below the par level, an entry is manually made on a pick-list for that nursing station including information identifying the nursing station, the drug name and its strength, and the quantity required to bring the nursing station up to par level for the particular drug. Once all of the disposition records for all of the nursing stations have been processed in this manner, the technician takes the pick-list to the drug safe.

The technician gathers the required quantity of each drug listed on the pick-list for a particular station, one drug at a time. If the required quantity of a drug is contained in a box, the technician writes the nursing station and current date on the box. Otherwise, the drugs are placed in a resealable bag and the nursing station and date are handwritten on a label and the label affixed to the bag. The drug is then checked off from the pick-list for that particular nursing station. When all of the drugs for a nursing station have been picked, the drugs are bundled together with a rubber band and placed aside while the technician picks the drugs for the remaining nursing stations.

When the drugs have been picked for all of the nursing stations, the technician then fills out a Stock Replacement Work Sheet which consists of a large grid with rows representing each nursing station and columns representing each drug that is tracked. For each nursing station on the pick-list and for each drug required for that particular nursing station, the quantity of the drug picked or removed from the safe is recorded in the grid cell in association with the particular nursing station and drug. Then for each drug on the Stock Replacement Work Sheet, the technician adds the entries for the drug and places a total in the last row in association with the drug column. The Stock Replacement Work Sheet is then used to update the Drug Logs for each drug that was picked.

In accordance with government regulations, each drug has an individual Drug Log that records each transaction that occurs involving the drug. In order to update the Drug Logs for each drug that was picked, the log for the particular drug must be manually retrieved and the following information entered: the current date, the total amount picked as indicated on the Stock Replacement Work Sheet, the technician's initials, a code representing the destination of the drug, and a new balance which is calculated by taking the last balance of the drug and subtracting the amount picked.

Thereafter, a physical inventory of the drug is performed whereby the technician counts the quantity of the drug remaining in the safe. The technician then compares the counted quantity remaining to a balance recorded in the Drug Log for the particular drug. If there is a discrepancy, the technician must find the cause of the discrepancy, i.e. math or entry error and correct it. If the technician cannot determine the cause of the discrepancy, a discrepancy report is filed. It is also not uncommon for drugs to be picked from the safe at irregular intervals before or after the picking process occurs. In these situations, because of the typical urgency to deliver the drug to its intended destination, the Drug Log may not be accurately updated resulting in discrepancies.

When drugs are to be added to the drug safe from a wholesaler or are returned from a nursing station, they must also be recorded on the drug logs. For each drug received, the drug is counted and the Log for the drug is obtained. The technician then manually records the current date, the total amount of the drug counted as being received, the technician's initials, the source of the drugs i.e., the identity of the nursing station or the wholesaler, and a new balance which is calculated by taking the last balance of the drug and adding the amount received. A physical inventory of the drug is then performed. The technician then compares the recorded balance on the Drug Log to the balance resulting from the physical inventory of the drugs. Again, if a discrepancy is found, the technician must find the cause of the discrepancy and correct it or file a discrepancy report.

Each month, the drugs in the safe are also examined to locate any that have passed their expiration date. Outdated drugs are removed from the area in the safe from which the drugs are dispensed to nursing stations and are placed in a separate location in the safe until they are disposed of. For each outdated drug that is removed to the separate disposal location in the safe, the Log for the drug is pulled and the following information recorded: the current date, the quantity of the drug being outdated, the technician's initials, a code representing the destination, i.e. the outdate location within the safe or a destruction location and a new balance which is calculated by taking the last balance of the drug and subtracting the amount being outdated. A physical inventory of the drug is then performed as discussed above with discrepancies either being corrected or being accounted for by the filing of a discrepancy report. An entry is also manually made in a Discarded Meds Drug Log for outdated drugs. This Log tracks the outdated drugs until they are disposed of and contains the same information as the regular Drug Logs. The manual entry of the required information by handwriting the entries or even by manually entering the information into a computer is expensive, labor intensive and is prone to inaccuracies requiring many hours to resolve and to report the discrepancies.

Automatic systems for dispensing drugs are known such as described in U.S. Pat. No. 5,762,235. However, these systems do not track the location of the drug.

BRIEF SUMMARY OF THE INVENTION

In accordance with the present invention, the disadvantages of prior methods for tracking drugs as discussed above have been overcome. The system and method of the present invention utilize a portable scanning and printing system for tracking drugs maintained at a location so as to minimize the manual entry of tracking data and automatically update the requisite records to improve the accuracy, speed and efficiency of the drug tracking.

More particularly, the portable scanning and printing system includes a memory for collecting data, a display, a printer and a number of input means including a barcode scanner, a keyboard or keypad, and a wireless communication interface. The wireless communication interface allows the portable scanning and printing system to communicate with a host system having a memory for storing drug tracking records wherein the host system automatically updates the drug tracking records from information transmitted thereto by the portable scanning and printing system.

The portable scanning and printing system is operated in accordance with the method of the present invention so as to receive user identification information from one of the input means; to receive from the scanner, scanned barcode data representing the identity of a drug maintained at the location; and to receive from the keyboard data confirming a quantity of a drug being added to or removed from the location. The portable scanning and printing system associates the data entered from the various input means and automatically transmits to the host system via the communication interface selective, associated information regarding the addition of the drug or the removal of the drug from the location so that the records at the host can be automatically updated. The information includes the user's identification, the destination or source, the identity of the drug and the quantity of the drug being added or removed. Any labels that are required are printed by the portable scanning and printing system from the information entered from the various input means during the drug tracking operation without the necessity to re-enter any data. The portable scanning and printing system automatically selects which associated information is to be printed and prints the labels at the location where they are needed. This operation of the portable scanning and printing system for tracking drugs maintained at a location drastically improves the speed and accuracy of tracking drugs.

In accordance with another feature of the present invention, the portable scanning and printing system is operated to receive from the keyboard, data representing a quantity of the drug that the user counts as remaining at the location, i.e. a user entered balance. The portable scanning and printing system verifies the user entered balance by wireless communication with the host system and the use of the host system's records. In particular, the user entered balance is compared to the balance data for the drug maintained in the host's stored drug tracking records. This comparison may be done by the portable scanning and printing system upon receipt of information representing a balance stored in the host's records or upon the updating of balance data stored in the portable system's memory. Alternatively, the comparison can be made by the host system in which case the host transmits the results of the comparison to the portable scanning and printing system which thereafter uses the results to verify the balance. The user entered balance is verified if the comparison results in a determination that the user entered balance matches the balance maintained in the host's records. If the user entered balance is not verified, the portable scanning and printing system allows the user to re-enter the counted quantity so that any counting errors can be immediately corrected. Alternatively, if a discrepancy is confirmed, the portable scanning and printing system determines the amount of the discrepancy and a discrepancy record is automatically transmitted to the host system.

In accordance with another feature of the present invention, the portable scanning and printing system automatically prompts the user to pick drugs identified by pick-list information received from the host system. After prompting the user to pick a particular drug, by displaying information identifying the drug to be picked for a particular destination, the user scans a barcode associated with the identified drug, the barcode typically being located on the shelf supporting the drug, or on a drug container. Upon receiving a scanned barcode representing the identity of a drug, the portable scanning and printing system compares the identity of the drug represented by the scanned barcode data to the identity of the drug received from the host system. If there is no match, an error message will be displayed for the user so as to advise the user that the wrong drug was scanned. By prompting the user for a particular drug and automatically verifying whether the user entered drug identity matches the drug that the system has prompted the user to pick, the present invention insures that the correct drugs are picked and that all of the drugs identified on the pick-list for a particular nursing station are picked so as to increase the accuracy, speed and efficiency of the operation.

The system and method of the present invention can be utilized to track drugs removed from a location with a pick-list or without a pick-list, to track drugs received at a location, to outdate drugs and to inventory drugs accurately and efficiently. These and other advantages and novel features of the present invention, as well as details of an illustrated embodiment thereof, will be more fully understood from the following description and drawings.

DETAILED DESCRIPTION OF THE INVENTION

Figure 1:
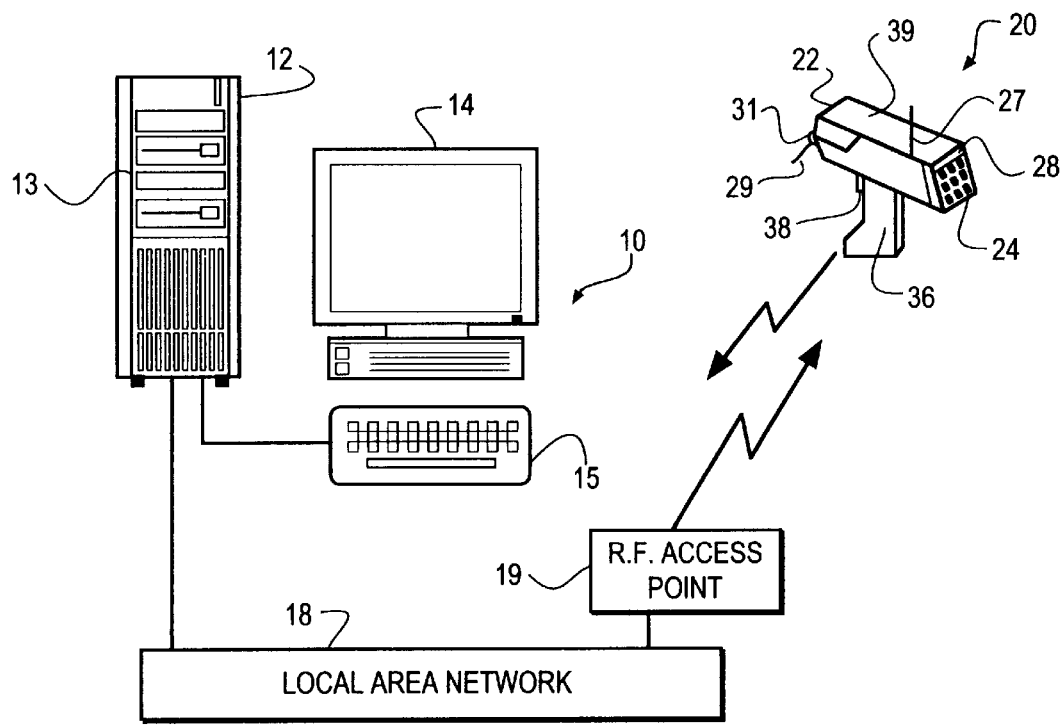
FIG. 1 is a block diagram of the system of the present invention including a portable scanning and printing system for tracking drugs maintained at a location and a host system to which the portable system communicates.

FIG. 1 illustrates a system for tracking drugs, including narcotics, at hospitals, clinics, pharmacies, etc. The system includes a P.C. based server 10 having a personal computer (P.C.) 12 or the like with associated memory 13, a display 14, a keyboard 15 and/or mouse. The P.C. 12 is coupled to a local area network (LAN) 18 that includes the capability of wireless communication. One example of a suitable local area network 18 is a token ring although other types of LANs can be used as well. A radio frequency access point 19 on the local area network allows the P.C. based server 10 to communicate i.e. transmit and receive, wireless communications with the portable barcode scanning and printing system 20. Whereas, the P.C. based server 10 with wireless communication capability forming a host system maintains drug tracking records in its associated memory, the portable barcode scanning and printing system 20 allows drug tracking data to be collected, verified and recorded with minimal input from the user so as to increase the speed and accuracy of the drug tracking operation.

Figure 2:
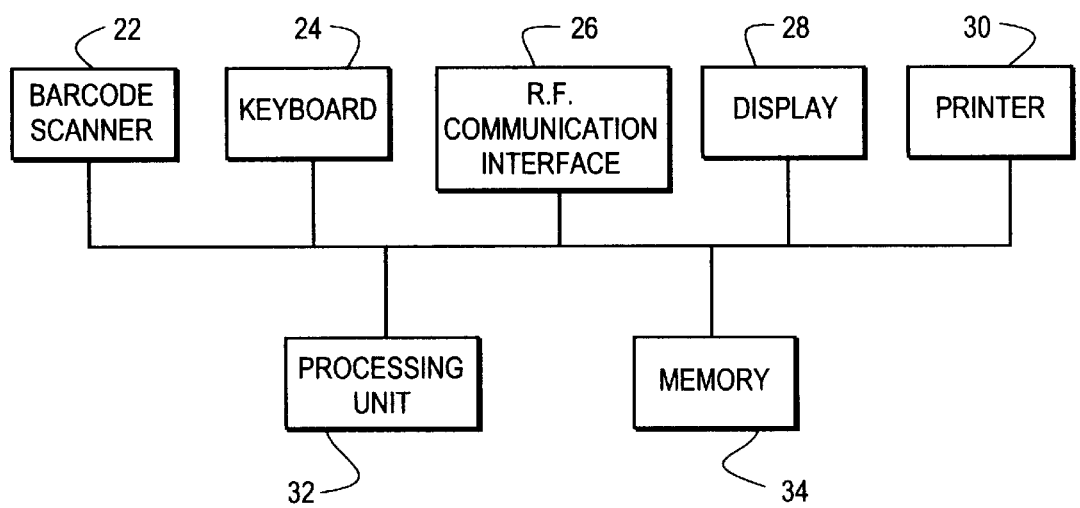
FIG. 2 is a block diagram of one embodiment of the portable scanning and printing system for tracking drugs as illustrated in FIG. 1.

The portable scanning and printing system 20 in accordance with one embodiment of the present invention as shown in FIGS. 1 and 2 is a hand-held integrated unit. Because it is portable, the user can track a drug and print barcoded labels therefrom at the drug's location on a shelf in the safe without moving to other locations to obtain Drug Logs or to use fixed location data entry and printing terminals. Because movement of the user away from the drug's shelf location is eliminated, numerous errors in the tracking process are eliminated and the accuracy and efficiency of the operation greatly increases.

The portable scanning and printing system 20 includes a number of input means for entering data into the system 20 including a barcode scanner 22, a keyboard 24 and a radio frequency communication interface 26. The barcode scanner 22 is operated to scan a barcode containing National Drug Code (NDC) information that identifies a drug, i.e. the drug's name and its strength. The keypad or keyboard 24 is used to enter alpha-numeric information into the system 20. The keyboard 24 can include a large number of keys or it can include a minimal number of keys one of which is used as a cursor or the like. The radio frequency (R.F.) communication interface 26 with associated antenna 27 includes a receiver and transmitter or transceiver to allow two-way communications between the portable scanning and printing system 20 and the host system 10 as discussed in detail below.

The portable scanning and printing system 20 includes a display 28 that is controlled to display prompts to the user to enter particular information so as to lead the user through a drug tracking operation in order to prevent the user from forgetting to enter information that is necessary to track a drug. The portable scanning and printing device 20 also includes a barcode printer 30 that is preferably a label printer. In the embodiment shown in FIG. 1, the printer portion 30 of the portable scanning and printing system 20 is a labeler that includes a label applicator 31 for applying labels 29 after they have been printed. The portable scanning and printing system 20 includes a processing unit 32 with one or more microprocessors for controlling the various input and output devices and for controlling the collection of data in the memory 34. In particular, the processing unit 32 collects data in the memory 34 by selectively associating input information received from two or more of the input means 22, 24 and 26. Such selective association of data in the memory 34 allows the processing unit to transmit and/or print selected portions of the associated data. Therefore, the portable scanning and printing system is an intelligent system and not merely an input and/or output device for the host system 10. In the preferred embodiment, the portable scanning and printing device has a handle 36 and a trigger 38 mounted on the handle so as to actuate the barcode scanner 22 and/or printer portion 30 of the system 20 in accordance with the software of the processing unit 32. In this embodiment, the barcode scanner 22 and printer 30 are contained within a housing 39 forming a single integrated unit that is portable. Details of a portable scanning and printing system such as described above are found in U.S. Pat. No. 5,483,624, entitled Programmable Hand Held Labeler, assigned to the assignee of the present invention and incorporated herein by reference. However, other configurations of the portable scanning and printing system 20 can be utilized in accordance with the present invention as well. For example, in another embodiment, a portable barcode scanner with data collection capabilities can be coupled via a hard wired connection to a portable or mobile printer. In another embodiment of the portable scanning and printing system 20 in accordance with the present invention, the portable scanner with data collection capabilities may communicate with a portable or mobile printer via RF communication. In still another embodiment, a scanner without data collection capabilities may be used with an intelligent printer capable of associating data received from the scanner portion, R.F. communication portion and the keyboard. Although the printer portion 30 of the portable scanning and printing system 20 need not necessarily be portable, in accordance with the present invention, a mobile printer is preferred since the mobility of the printer as well as the portability of the scanner allows the scanning and printing of labels to occur at the location of a particular drug in the drug safe. This feature allows the technician to complete the removal, addition and/or inventory of a single drug without the necessity of moving to another location within or outside of the safe before the tracking operation for that drug is completed. Thus, the efficiency as well as accuracy of the tracking system and method are greatly increased.

In accordance with the present invention, drugs may be picked i.e., removed from a location, based on a pick-list generated by the host system 10 or without the use of a pick-list as described in detail below. If a pick-list is to be used for the picking operation, a pick-list is generated by the P.C. 12 in accordance with the routine depicted in FIGS. 3A–3B. Upon entering the pick-list entry mode of operation, the P.C. 12 at a block 40 retrieves the various stations, in this example, nursing stations, from the Station records 42 stored in the P.C. server's memory and loads the retrieved stations into a selection box depicted on the display 14. The P.C. is responsive at bock 43 to a user's selection of a station depicted on the display 14 to retrieve, at block 44, the drugs assigned to the selected station from the Drug or Narcotics records 58 of the P.C. server's memory. At block 44 the P.C. 12 loads a pick list grid depicted on the display with the retrieved list of drugs for the selected station. At block 46, the P.C. 12 loads for each drug listed in the pick list grid the amount of the drug to be picked as indicated in the pick list records 48 previously stored for the station. Thereafter, the P.C. 12 proceeds to block 49 to determine whether new drugs are to be assigned to the station based on user selection of a displayed "Narcotics Button" at block 50. If so, the P.C. 12 proceeds to block 51 to execute the routine depicted in FIG. 3C.

Figure 3A:
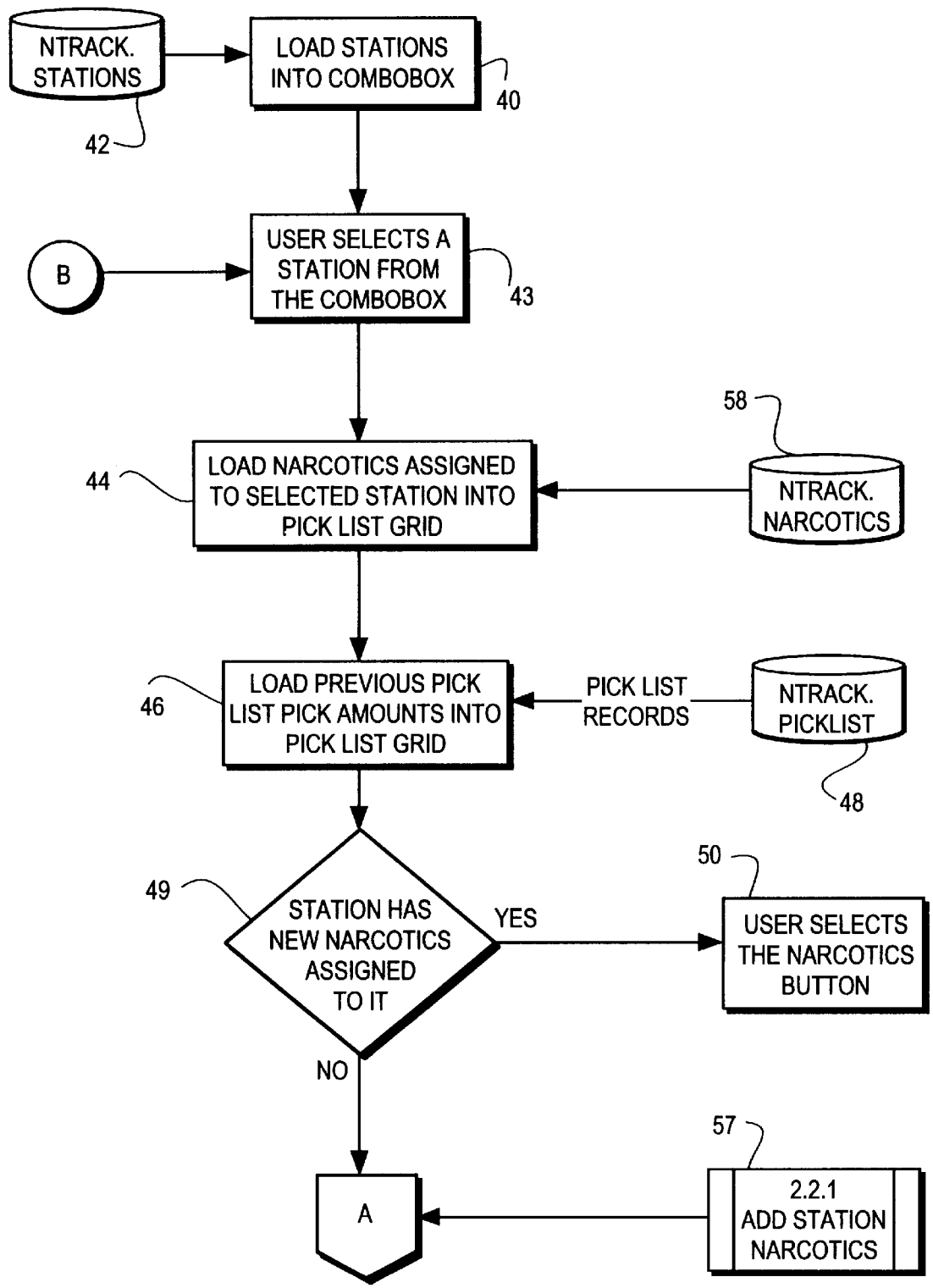
FIGS. 3A, 3B and 3C form a flow chart illustrating the operation of the host processing system in generating a pick-list.
Figure 3B:
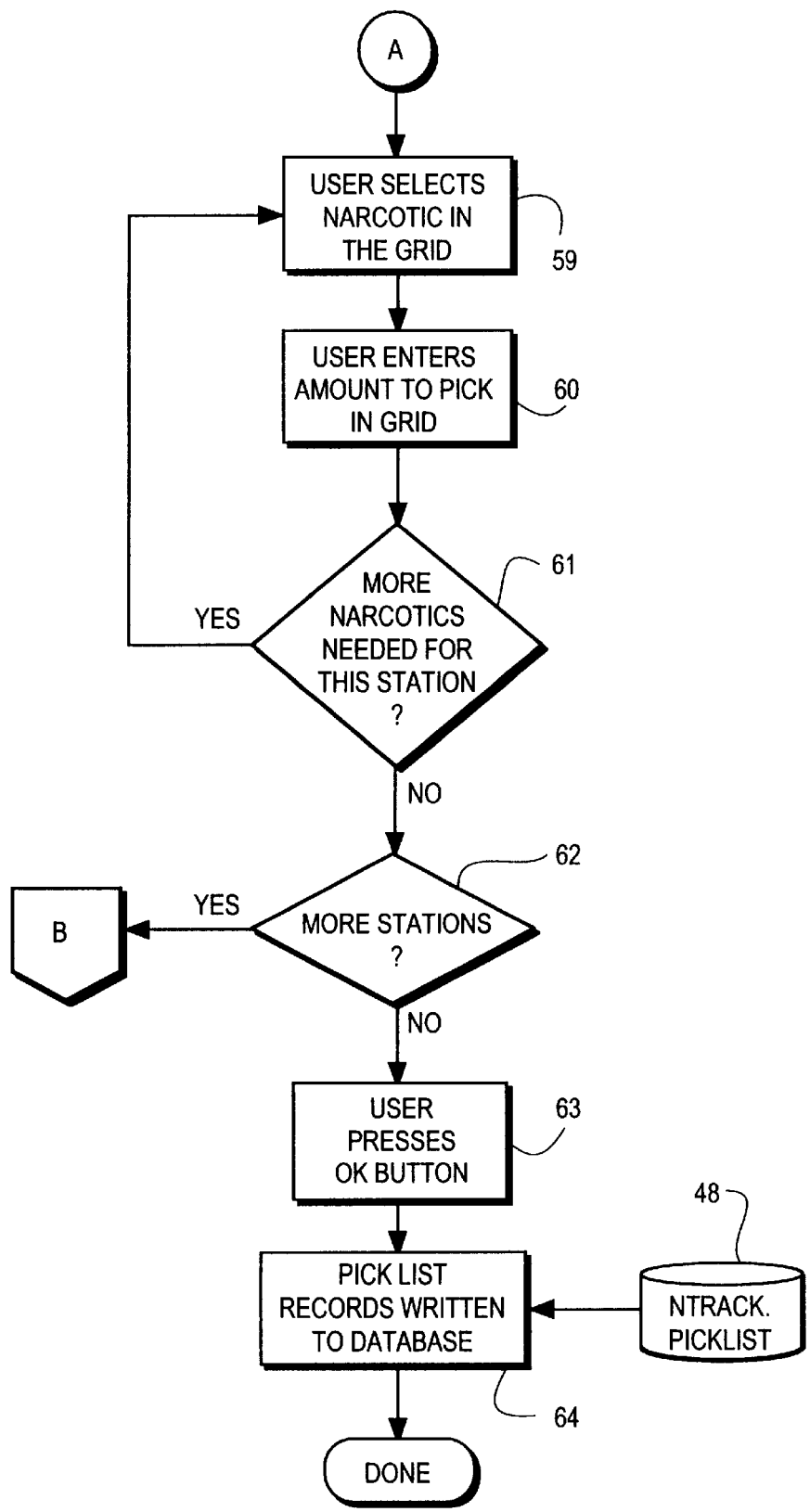
Figure 3C:
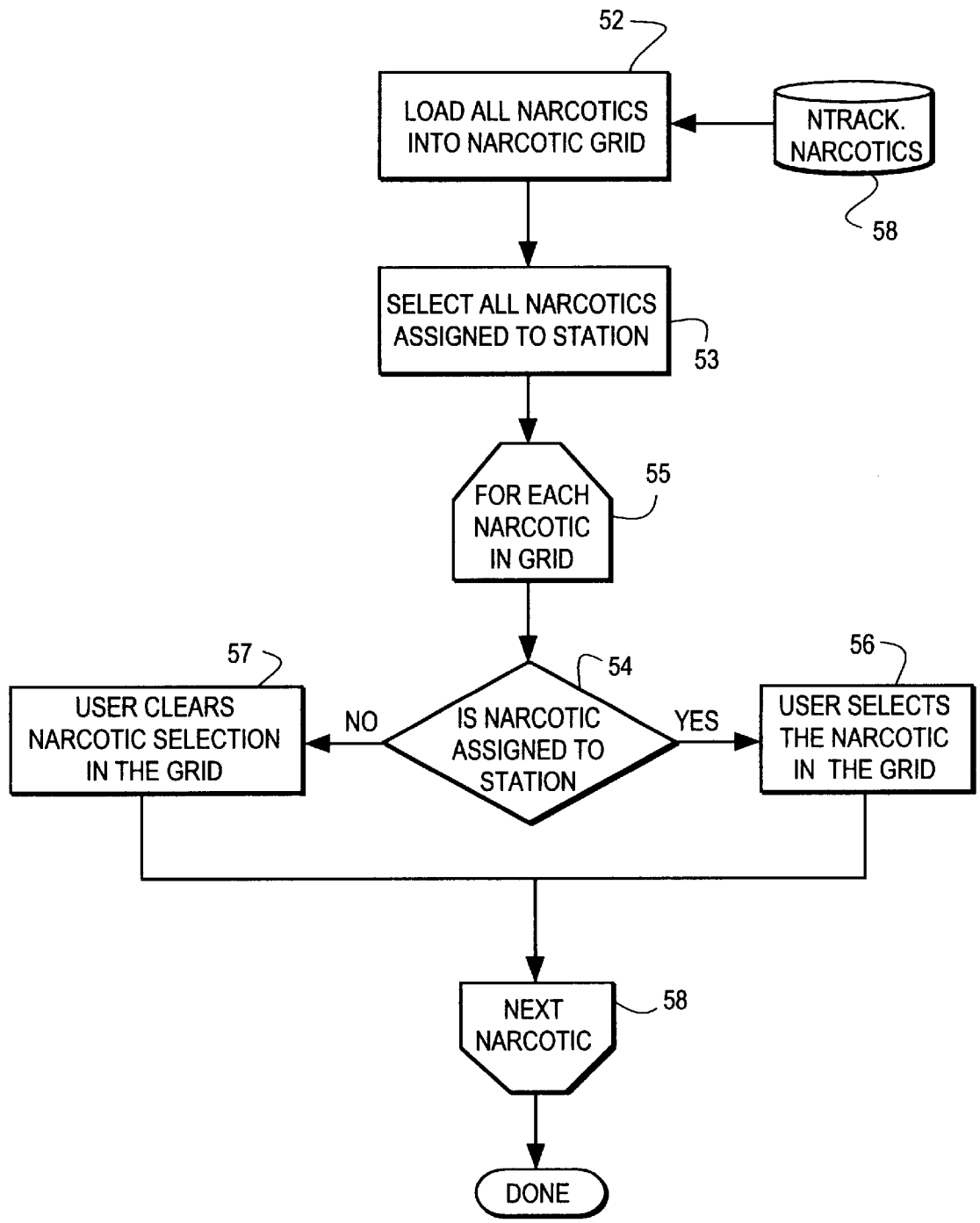

Upon entering the routine of FIG. 3C, the P.C. 12 loads at block 52 a list of selectable narcotics retrieved from the narcotics records 58 into a "Narcotic Grid" depicted on the display 14. At block 53, the P.C. 12 automatically selects all of the narcotics that were previously assigned to the station. Thereafter, for each drug depicted in the "Narcotics Grid" as determined at block 55, the P.C. 12 determines at block 54 whether or not it is to be assigned to the station. In particular, at block 56, the P.C. 12 is responsive to user selection of a drug in the grid to assign it to the station. Alternatively, if the P.C. 12 determines at block 57 that the user cleared the drug selection from the grid, the narcotic is not assigned to the station. At block 58, the P.C. 12 proceeds to the next narcotic listed in the "Narcotic Grid" to determine whether it is to be assigned to the station or not and continues until all of the necessary drugs have been assigned to the station. Thereafter, the P.C. 12 returns to the pick list entry routine at block 59 of FIG. 3B.

At block 59, the user selects a narcotic in the pick list grid depicted for the station. At block 60 the user acknowledges as correct the amount of the drug to be picked in the grid if it is the same as indicated by the pick list records 48 and loaded into the grid at block 46. Alternatively, if a new amount is to be entered for the drug, the user enters the new amount of the drug to be picked into the displayed grid at block 60. At block 61, the P.C. 12 determines whether more narcotics are to be picked for the particular station and if so, proceeds back to block 59. When the user finishes the pick list for a particular station, the P.C. proceeds to block 62 to determine whether pick lists are to be generated for other stations. If so, the P.C. 12 proceeds back to block 43 so that the process can be repeated. When the user has finished the pick list entry process as indicated by the user selecting a displayed "OK button" at block 63, the P.C. 12 proceeds to block 64. At block 64, the pick list records generated during the operation of the flow charts of FIGS. 3A–3C are written to the database pick list records 48.

Figure 4:
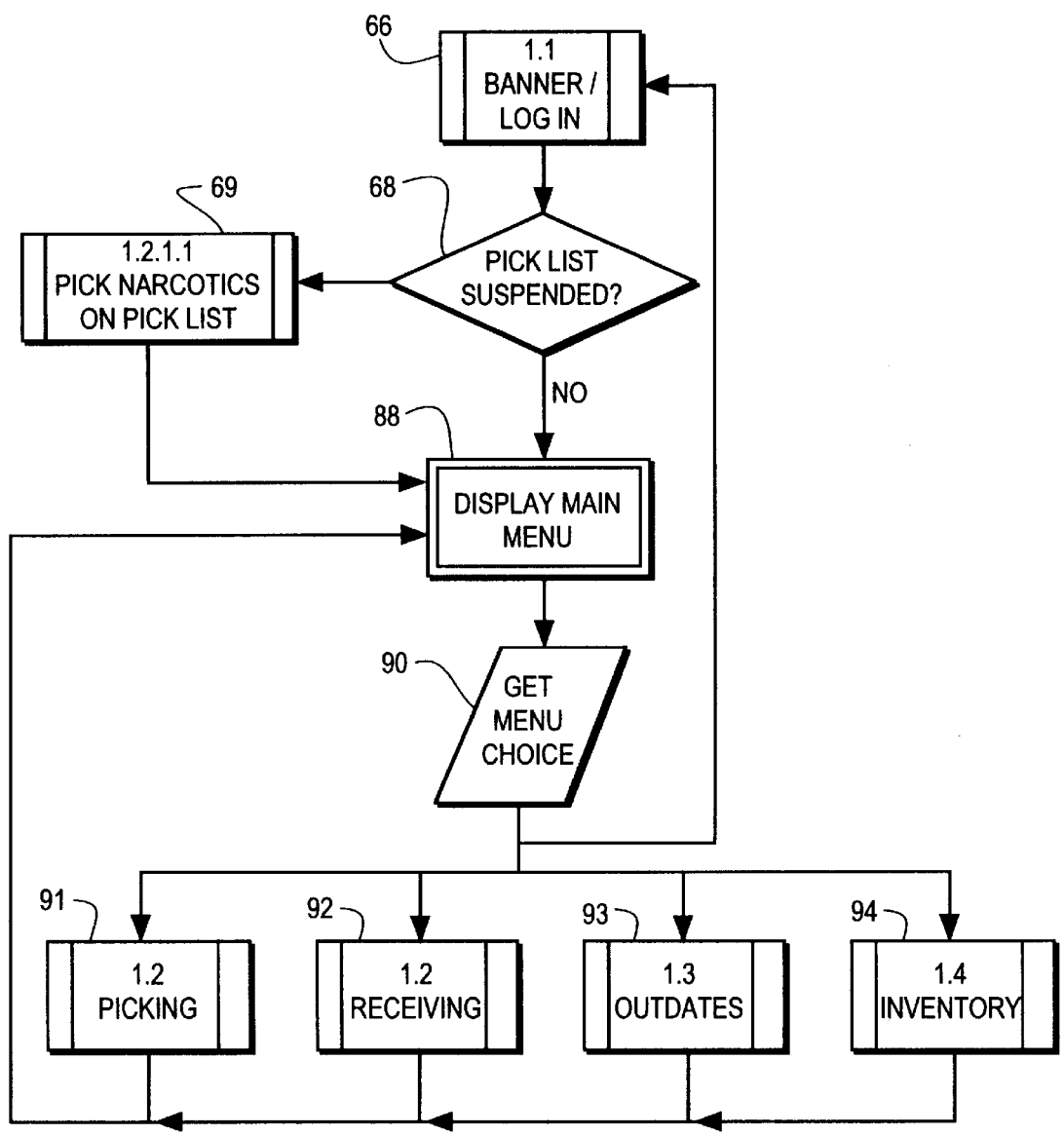
FIG. 4 is a flow chart illustrating various operations of the portable scanning and printing system for tracking drugs.
Figure 5:
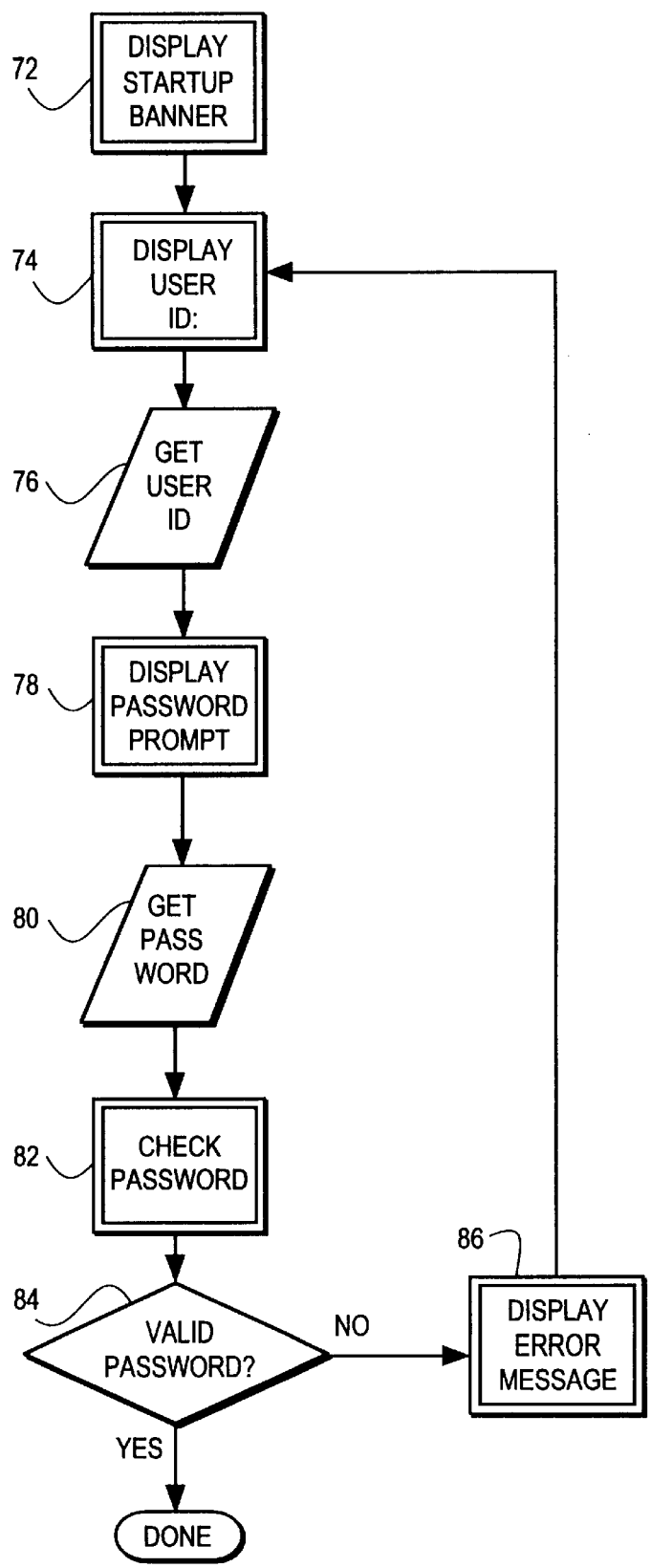
FIG. 5 is a flow chart illustrating a user login operation of the portable scanning and printing system.

In order to use the portable scanning and printing system 20 for tracking drugs at a location, the user starts up the system 20 in a banner/log in mode at block 66 of FIG. 4. This mode as depicted in FIG. 5 starts with the processing unit 32 depicting a start up or introduction display screen on the display 28 at a block 72. Thereafter, the processing unit 32 displays a prompt at a block 74 for the user to enter his identification. The user may enter his identification via the keyboard 24 or if the user has a badge or the like with a barcoded identification, the user can enter his identification using the barcode scanner 22. The processing unit 32 receives the entered user identification at a block 76 and thereafter, prompts the user at a block 78 via the display 28 to enter the user's password. The processing unit 32 at block 82 checks the entered password to determine whether the password is valid or not at a block 84. If the password is determined at block 84 to be invalid, the processing unit 32 controls the display 28 to display an error message at block 86, the processing unit 32 thereafter returning to block 74. If the user has entered a valid password, the processing unit 32 returns to the routine depicted in FIG. 4 at block 68. If the processing unit determines at block 68 that a pick list has been suspended, it will proceed at block 69 to the routine depicted in FIGS. 6A–6C. Otherwise, the processing unit proceeds to block 88.

The processing unit 32 at block 88 causes the main menu of the system to be depicted on the display 28. The main menu depicts the various drug tracking operations that can be performed with the portable scanning and printing system 20 including picking operations, receiving operations, out-date operations and an inventory operation. Thereafter, the processing unit 32 receives at a block 90 the user's choice selected via the keyboard 24 and executes the routine 91, 92, 93 or 94 associated with the selected operation.

Upon entering the picking routine at block 91, the processing unit 32 controls the display 28 to depict various picking operation menu choices including a Pick-List Picking operation and No Pick-List Picking operation for the user's selection. If the user selects the option to pick drugs in accordance with a pick-list, the processing unit executes the routines depicted in FIGS. 6A–6C and FIGS. 7A–7D. If the user selects the option to pick drugs without a pick-list, the processing unit executes the routine depicted in FIGS. 9A–9E.

Figure 6A:
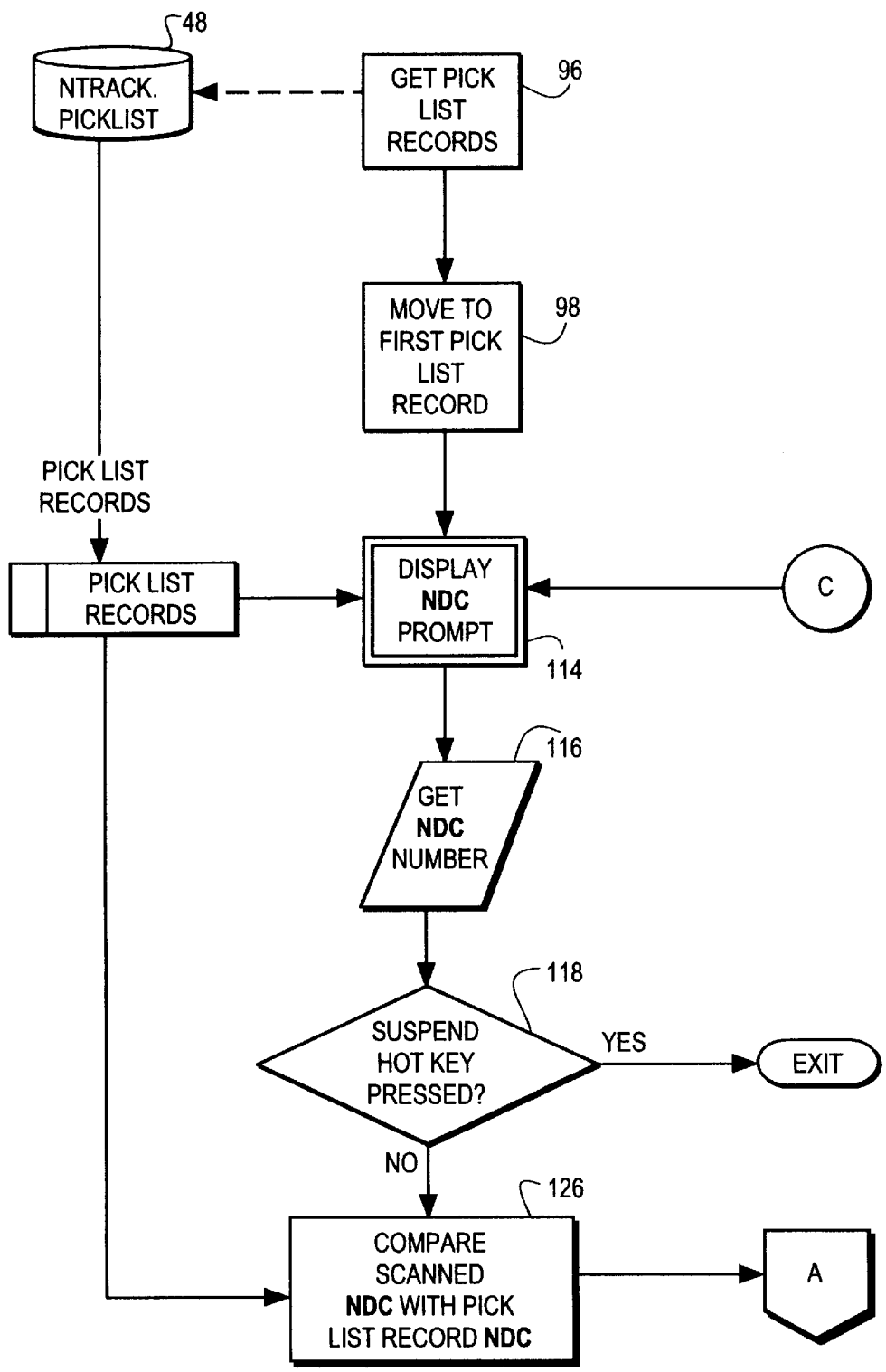
FIGS. 6A, 6B and 6C form a flow chart illustrating the operation of the portable scanning and printing system when drugs are picked from a pick-list.
Figure 6B:
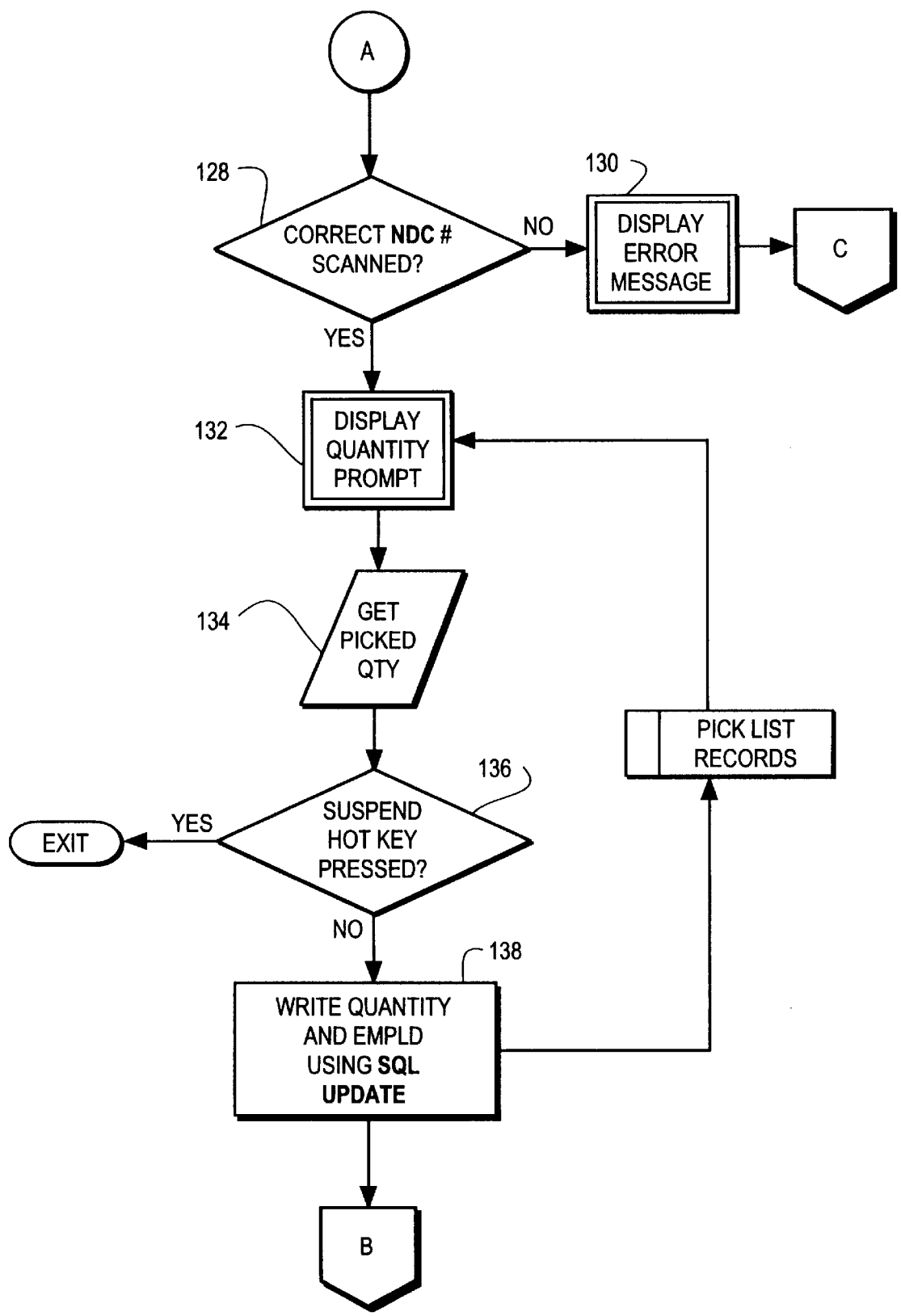
Figure 6C:
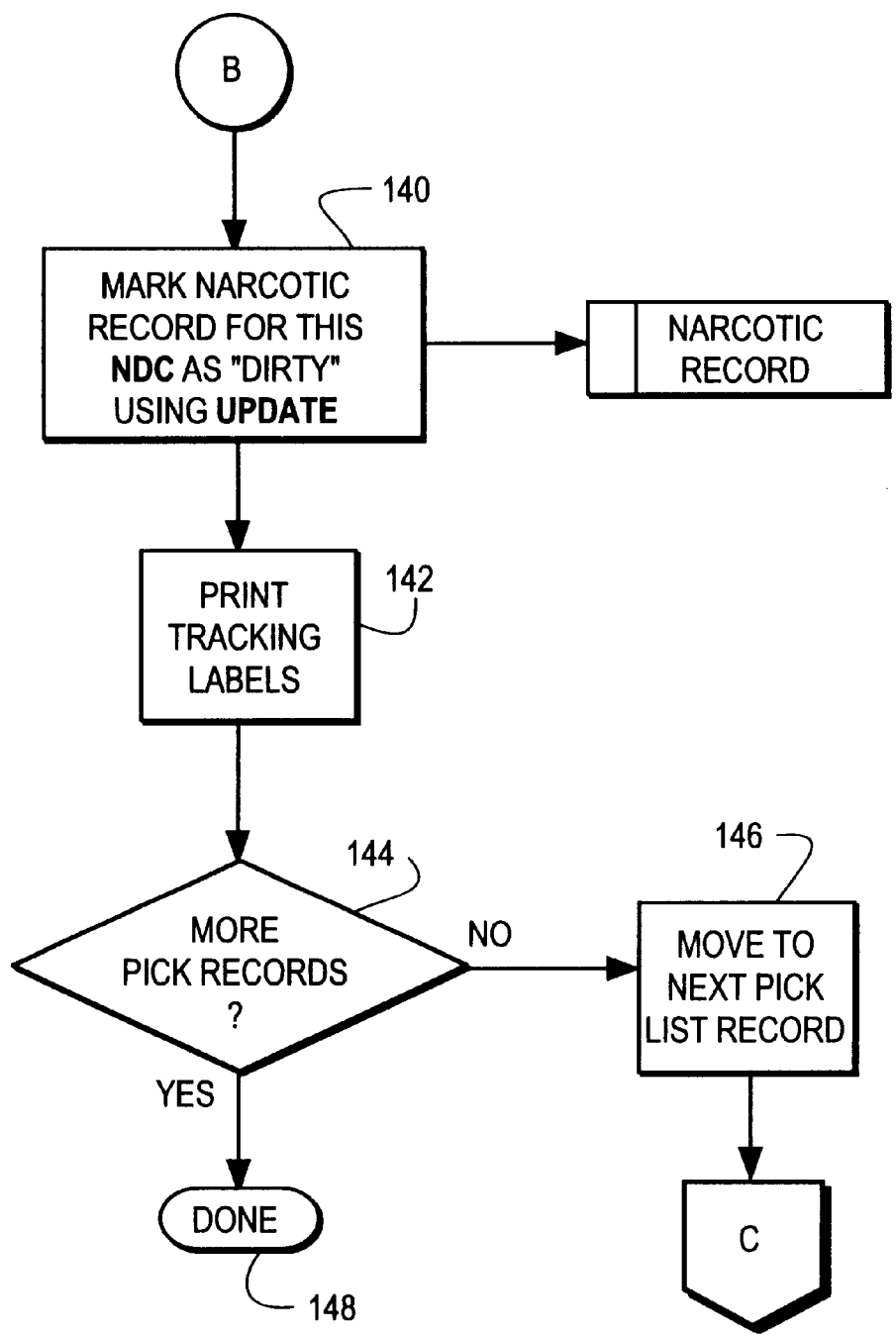
Figure 7A:
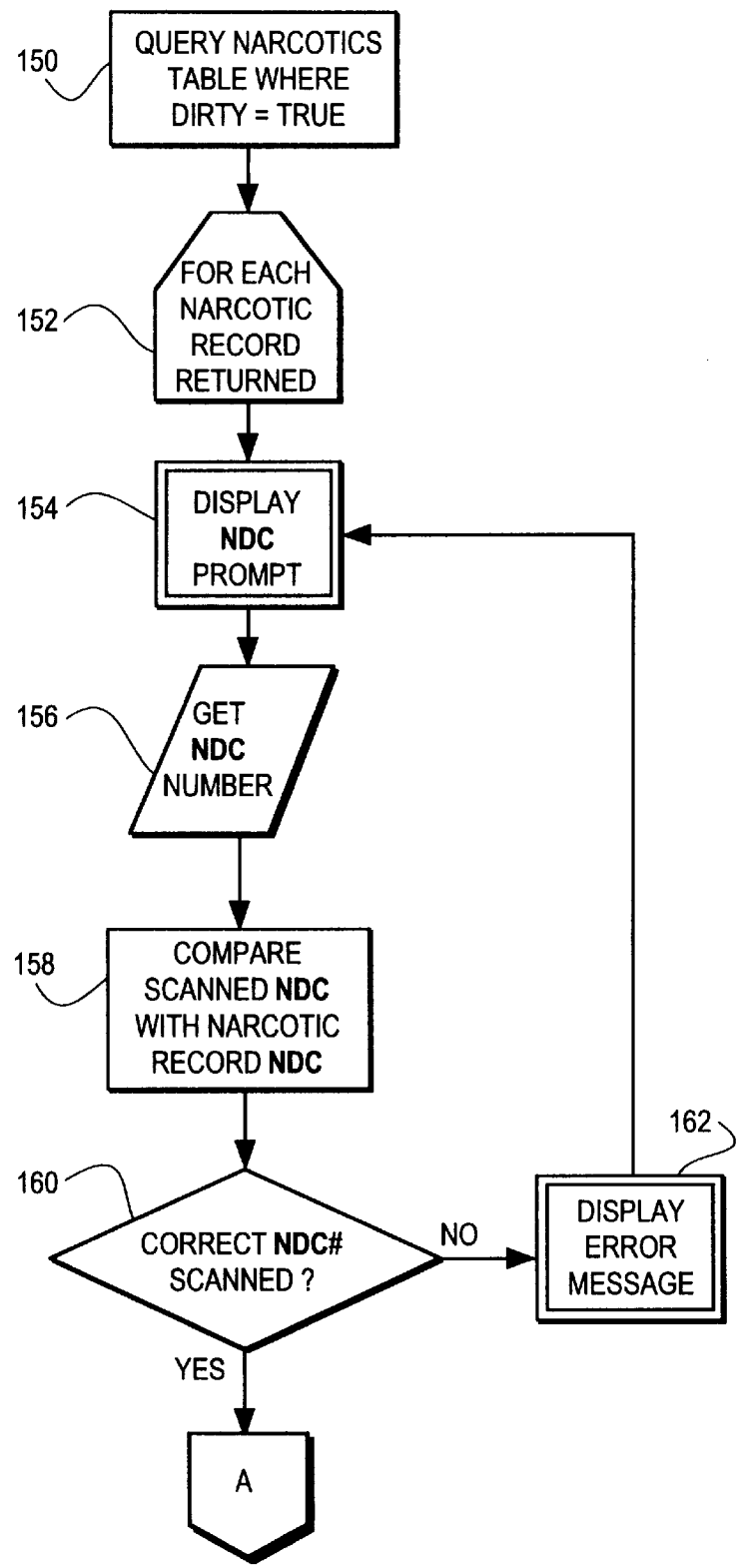
FIGS. 7A, 7B, 7C and 7D form a flow chart illustrating an inventory operation of the portable scanning and printing system for drugs picked from a pick-list.
Figure 7B:
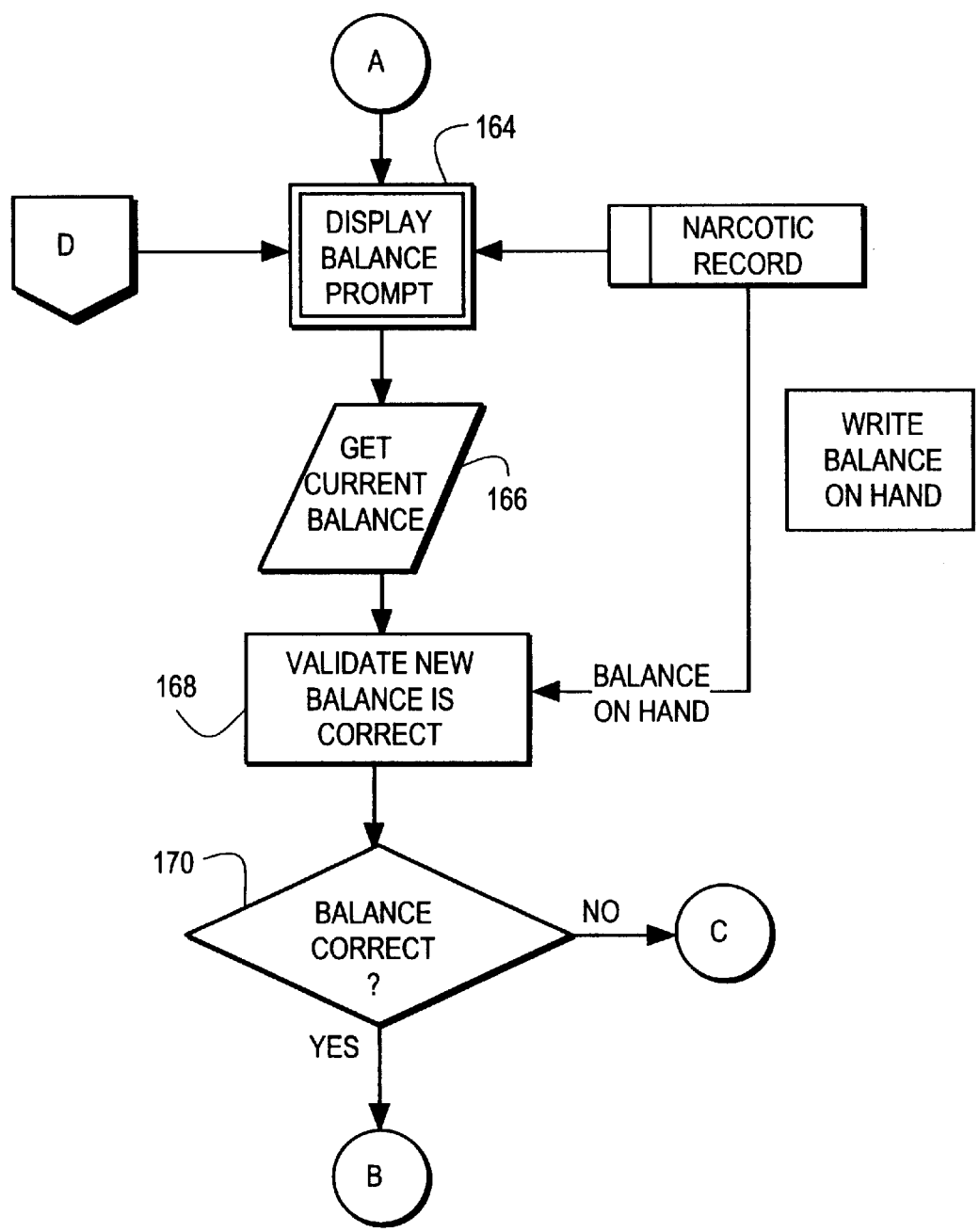
Figure 7C:
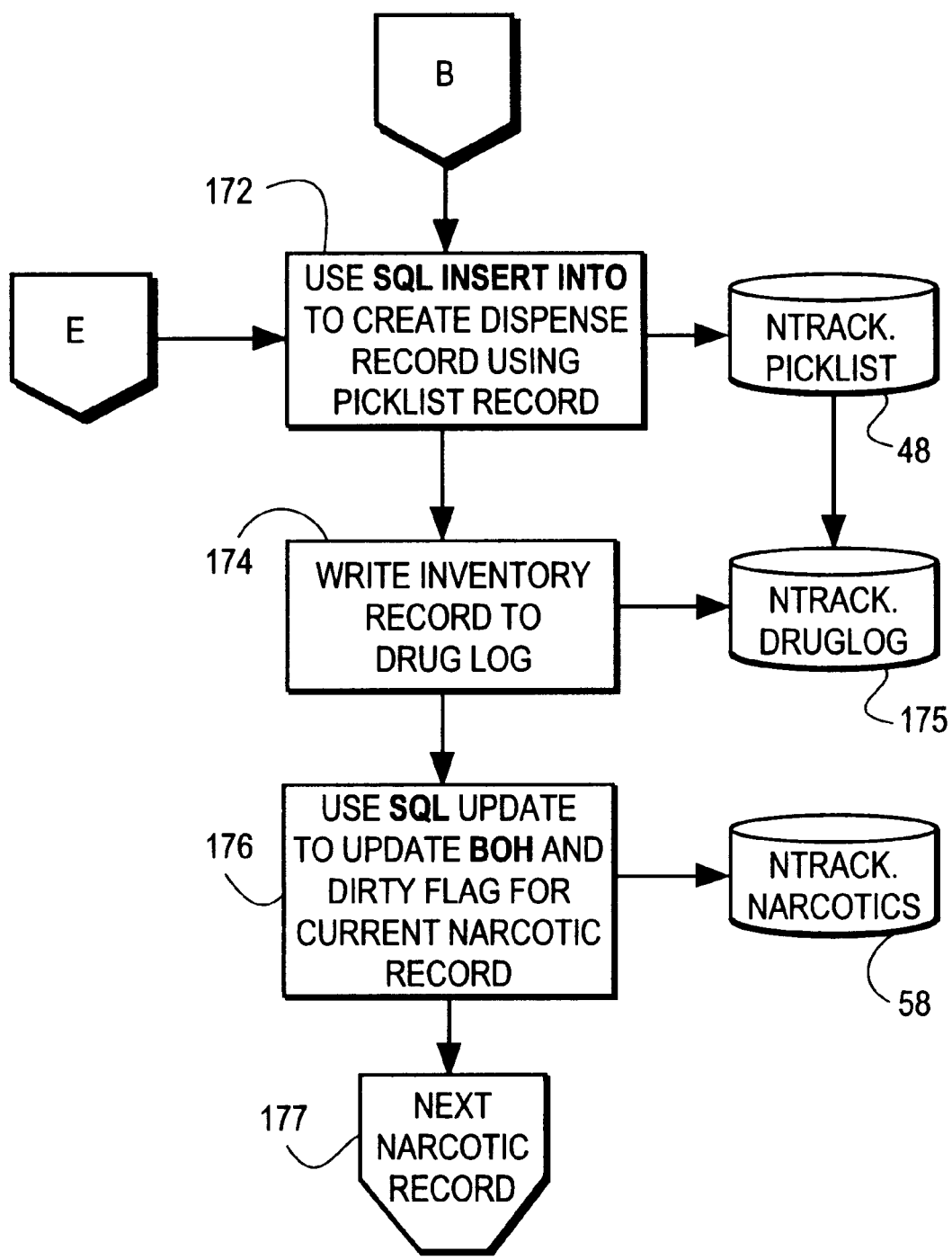
Figure 7D:
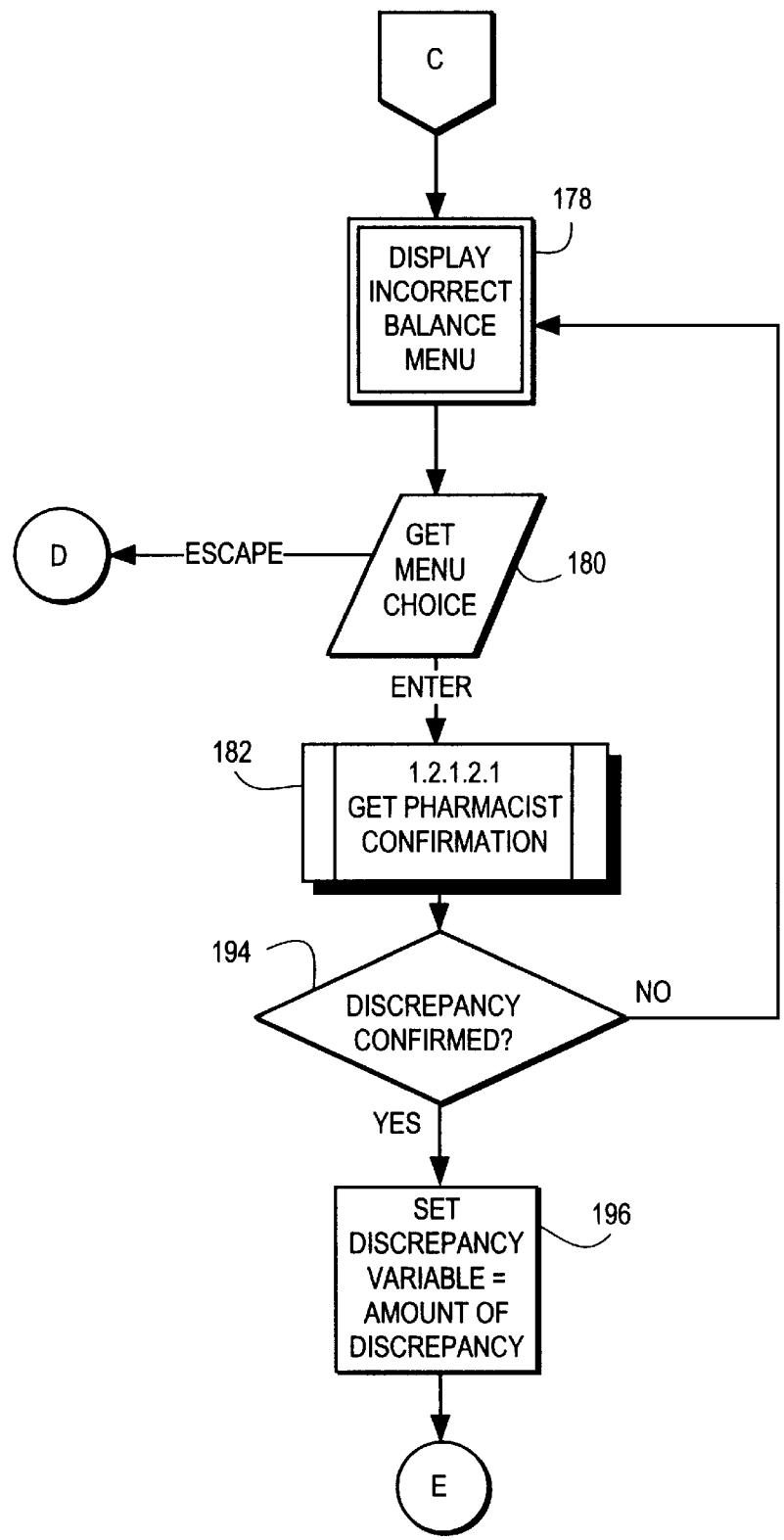

Upon entering the Pick-List Picking routine depicted in FIGS. 6A–6C, the processing unit 32 eat a block 96 retrieves one pick-list record from the host system's Pick-List records 48. After receiving at block 98, the pick-list record which contains the identity of a station representing the destination of the drug being a-picked, the identity of a drug including its strength and the quantity of the drug to be picked for that particular station, the processing unit 32 proceeds to block 114. At block 114, at the start of a picking operation for a particular drug, the processing unit 32 displays information identifying the drug to be picked for a particular nursing station to prompt the user to pick the correct drug. This prompt may include National Drug Code (NDC) information i.e., information identifying the name of the drug and its strength. In response to the display of the NDC prompt at block 114, the user scans a barcode, typically contained on a shelf supporting the drug on a drug container itself, where the barcode represents the drug identified in the displayed prompt. At block 116, the processing unit 32 receives from the barcode scanner 22 the data representing the scanned barcode including the NDC. Thereafter, the processing unit determines whether the suspend key of the keyboard 24 has been actuated at a block 118. If so, the processing unit 32 exits the routine. If the suspend key was not pressed as determined at block 118, the processing unit 32 proceeds from block 118 to block 126. At block 126, the processing unit compares the scanned NDC data received at block 116 with the NDC data contained in the pick-list record retrieved from the host system 10. At block 128, the processing unit 32 determines whether these two NDCs match and if not, the processing unit at block 130 displays a message to the user on the display 28 indicating that the user has scanned the wrong NCD code. This feature warns the user that he was about to pick the wrong drug and thus increases the accuracy of the picking operation and thus the drug tracking as well. After displaying the error message at block 130, the processing unit will thereafter return to block 114 to prompt the user via the display 28 to pick the correct drug and associated strength as indicated on the pick-list.

If the processing unit 32 determines at block 128 that the scanned NDC matches the NDC in the pick-list record received from the host system, the processing unit proceeds from block 128 to block 132. At block 132, the processing unit 32 controls the display 28 to depict a message to the user to prompt the user to enter the quantity to be picked. This prompt will actually display the quantity from the pick-list so as to advise the user of the quantity that the pick-list records indicate should be picked for a particular nursing station. However, the user has the option to select the displayed quantity for picking or to enter a new quantity. At block 134, the processing unit 32 retrieves from the keyboard 24 the quantity of the drug entered by the user as being picked. It is noted, the value that may be retrieved may represent an actual numeric quantity or if the user selects the quantity displayed at block 132, the received quantity information may actually be represented by an indication that an enter key or the like has been pressed indicating to the processing unit 32 that the displayed quantity has been selected by the user and is the "picked" quantity.

After receiving the quantity being picked by the user at block 134, the processing unit 32 proceeds to block 136 to determine whether the suspend key of the keyboard 24 has been actuated and if so, the processing unit 32 exits the routine. If the suspend key was not pressed, the processing unit proceeds from block 136 to block 138. At block 138, the processing unit updates the pick-list record in the memory 34, by associating the user entered quantity being picked with the pick-list record information received from the host system for the particular drug picked. From block 138, the processing unit proceeds to block 140. At block 140, the processing unit 32 sets a flag in a Narcotic table stored in the memory 34 indicating that this drug was picked. At block 140, the processing unit also updates the narcotic record for the drug in the memory 34, the record originally received from the host system's Narcotic records 58. When updating the Narcotics record in the memory 34, the processing unit 32 automatically calculates a balance on hand by subtracting the quantity received at block 134 from the old balance in the record. Thereafter, the processing unit proceeds to block 142 from block 140.

At block 142, the processing unit 32 causes the printer 30 to print selected information associated with the picked drug by the processing unit 32 in the memory 34. The information printed on the label includes the intended destination of the drug which is automatically printed to prevent the drug from being sent to the wrong location. The information printed on the label also includes the barcoded NDC data for the drug so that the drug can be tracked by a portable scanning and printing system 20 at its destination location. The automatic continuation of the tracking data throughout various locations of a hospital via the use of multiple portable scanning and printing systems all in communication with the host allows tight control over drugs and current as well as accurate drug tracking records. It is noted, that the user may enter the number of tracking labels to be printed via the keyboard 24 or alternatively, this information may be stored in association with the pick-list data. For example, one label may be printed to be applied to a box containing the picked quantity of a particular drug, or multiple labels may be printed for application to individual drug containers if the drug is so packaged. After the processing unit 32 controls the printer 30 to print the requisite number of labels, the user applies the labels directly to the packaging for the drugs and then continues the picking operation. The processing unit 32 determines at block 144 whether there are more pick records by querying the host system 10. If the host system indicates that there are more pick records, the portable barcode scanning and printing system will receive the next pick-list record at a block 146 and return to block 114 to display the NDC prompt associated with the next pick-list record.

After picking the drugs for each station on the pick-list as determined at block 144, the processing unit proceeds from block 148 of FIG. 6C to the routine depicted in FIGS. 7A–7D so as to inventory the drugs picked on the pick list. This inventory operation automatically determines whether the quantity of a drug remaining after having been picked for one or more stations matches a balance on hand quantity automatically calculated by the system 20 as the drugs on the pick-list were being picked. In order to inventory the drugs picked in accordance with a pick-list, the processing unit 32 looks to the Narcotics table stored in the memory 34 to determine which of the drugs were marked picked at block 140. For each of the drugs that were marked as picked at block 140 as indicated at block 152, the processing unit 32 implements the remaining steps depicted in the flow charts of FIGS. 7A–C. First, the processing unit controls the display 28 to depict a message to prompt so as to prompt the user to scan a barcode for the displayed NDC information including drug identity and strength. Thereafter, at block 156, the processing unit receives the scanned NDC data from the barcode scanner and proceeds to block 158 to compare the scanned NDC data with the NDC data contained in the Narcotic record stored in the memory 34 for the drug marked as having been picked and identified in the NDC prompt at block 154. At block 160, the processing unit determines whether there is a match between the scanned NDC information and the expected NDC data. If there is not a match, the processing unit 32 depicts an error message at block 162 on the display 28 and proceeds back to block 154 to prompt the user to scan the correct barcode associated with the drug from the pick list being inventoried. If there is a match as determined at block 160, the processing unit 32 proceeds to block 164 to display a balance prompt message. The balance prompt message prompts the user to count the quantity of the drug associated with the scanned NDC remaining at the location after a quantity has been picked, i.e. removed in accordance with the pick-list. After receiving the user entered balance at block 166, the processing unit 32 proceeds to block 168 to determine whether it is the same as the balance calculated and updated by the portable scanning and printing system 20 when executing block 140 each time the drug was picked for a different station on the pick list. If the balance is determined to be correct at block 170 by the unit 32 comparing the user entered balance and the balance on hand stored in memory 34 to determine if they match, the processing unit proceeds to block 172; however, if the balance is not correct, the processing unit proceeds to block 178 as discussed below.

At block 172 the processing unit 32 creates a dispense record in the memory 34 using the pick-list record maintained in the memory 34 where the dispense record confirms the removal of a particular drug from the location. The dispense record identifies the drug including its strength, the quantity removed i.e. dispensed, and the destination of the drug after it was removed from the location. At block 172, the dispense record is also transmitted via the communication interface 26 to the host system so that the host system can update its pick-list records 48 in its memory. From block 172, the processing unit proceeds to block 174. At block 174, the processing unit writes an inventory record for the particular drug indicating the quantity of the drug remaining at the location in the memory 34 and transmits the information to the host system so that the Drug Log memory 175 maintained at the host 10 may be updated with the inventory records from the portable scanning and printing system and from the pick-list records maintained at the host. From block 174, the processing unit 32 proceeds to block 176 to update the balance on hand in the narcotics record of the memory 34 and the flag in the Narcotics table for the picked drug to indicate that the balance for this drug has been checked and inventoried. The portable scanning and printing system at block 176 also transmits information to the host system to update the Narcotics records contained in the narcotic record memory 58. Thereafter, the processing unit at 177 returns to block 152 to inventory the next drug with the flag still set as indicating that the drug was picked via the pick list but that the balance was not inventoried as of yet.

If the balance received from the user at block 166 is determined by the processing unit 32 to be incorrect at block 170, the processing unit proceeds to block 178 from block 170 to control the display 28 to display an Incorrect Balance Menu. If the user determines that the remaining quantity of the drug was correctly counted and correctly entered into the system 20, the user selects an option to obtain a pharmacist's confirmation of a discrepancy. Upon receiving the selection of pharmacist's confirmation, the processing unit proceeds to block 182 to execute the routine depicted in FIG. 8.

Figure 8:
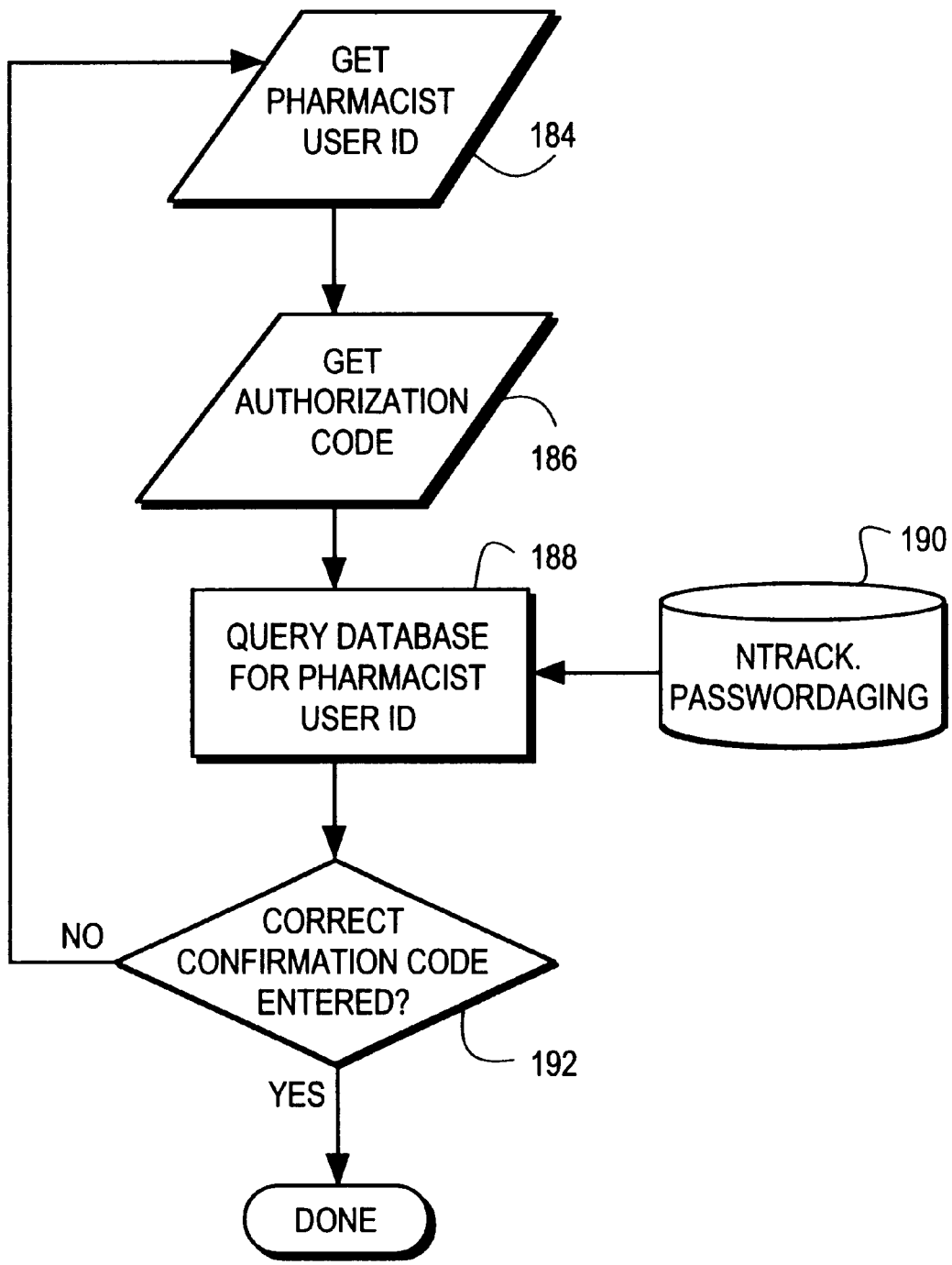
FIG. 8 is a flow chart illustrating an operation of the portable scanning and printing system in obtaining pharmacist confirmation.
Figure 9A:
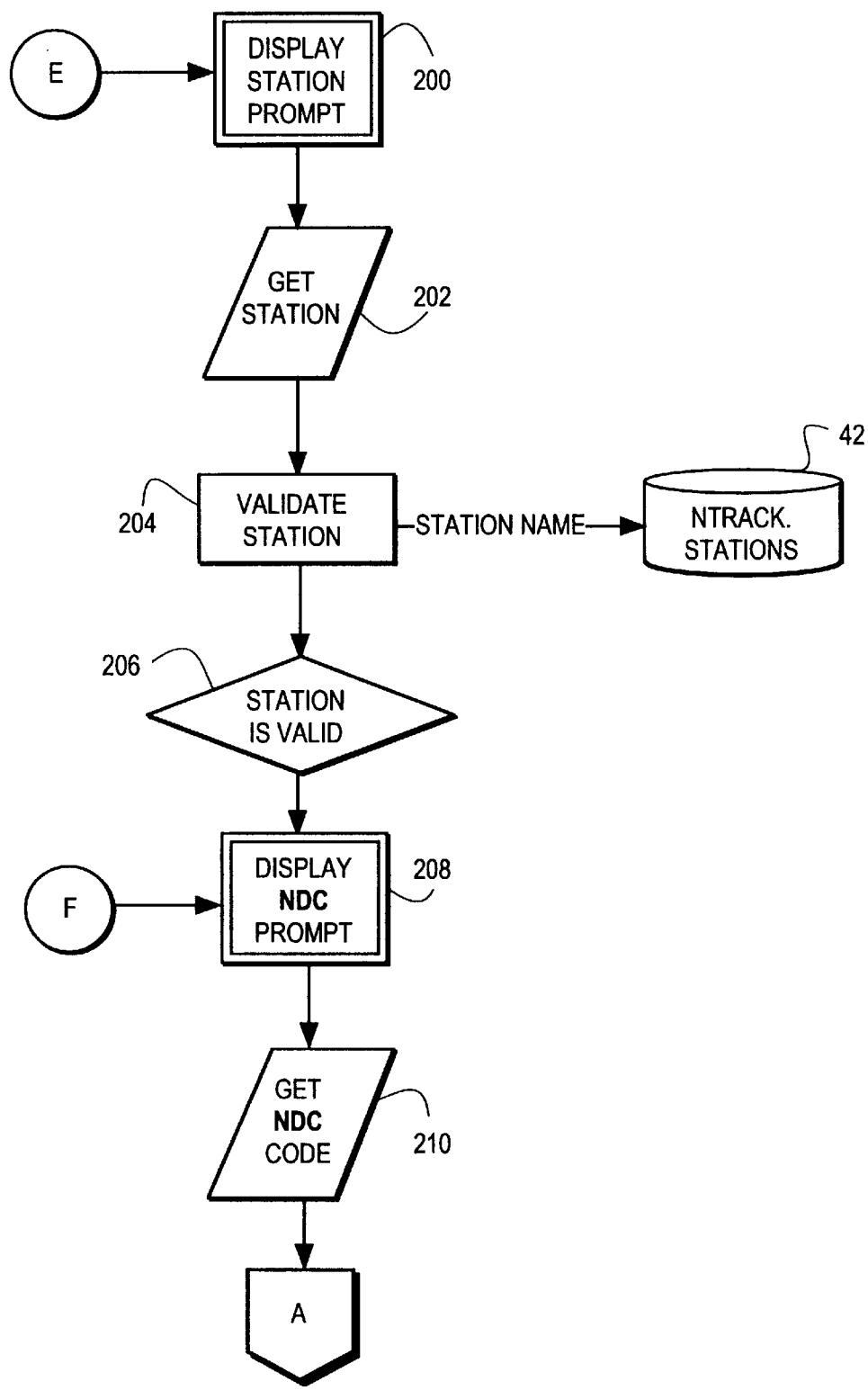
FIGS. 9A, 9B, 9C, 9D and 9E form a flow chart illustrating an operation of the portable scanning and printing system for picking drugs not on a pick list and for receiving drugs.
Figure 9B:
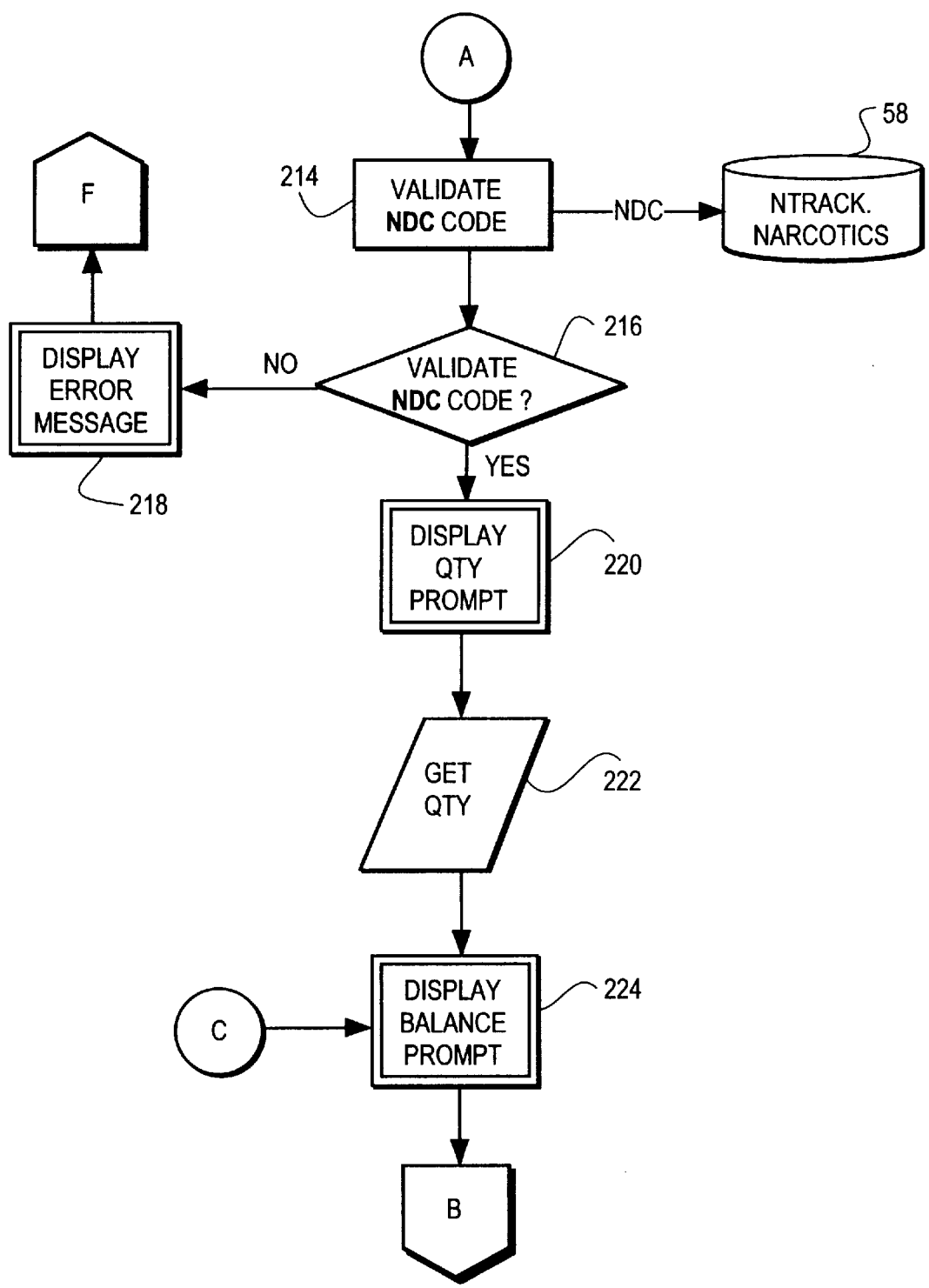
Figure 9C:
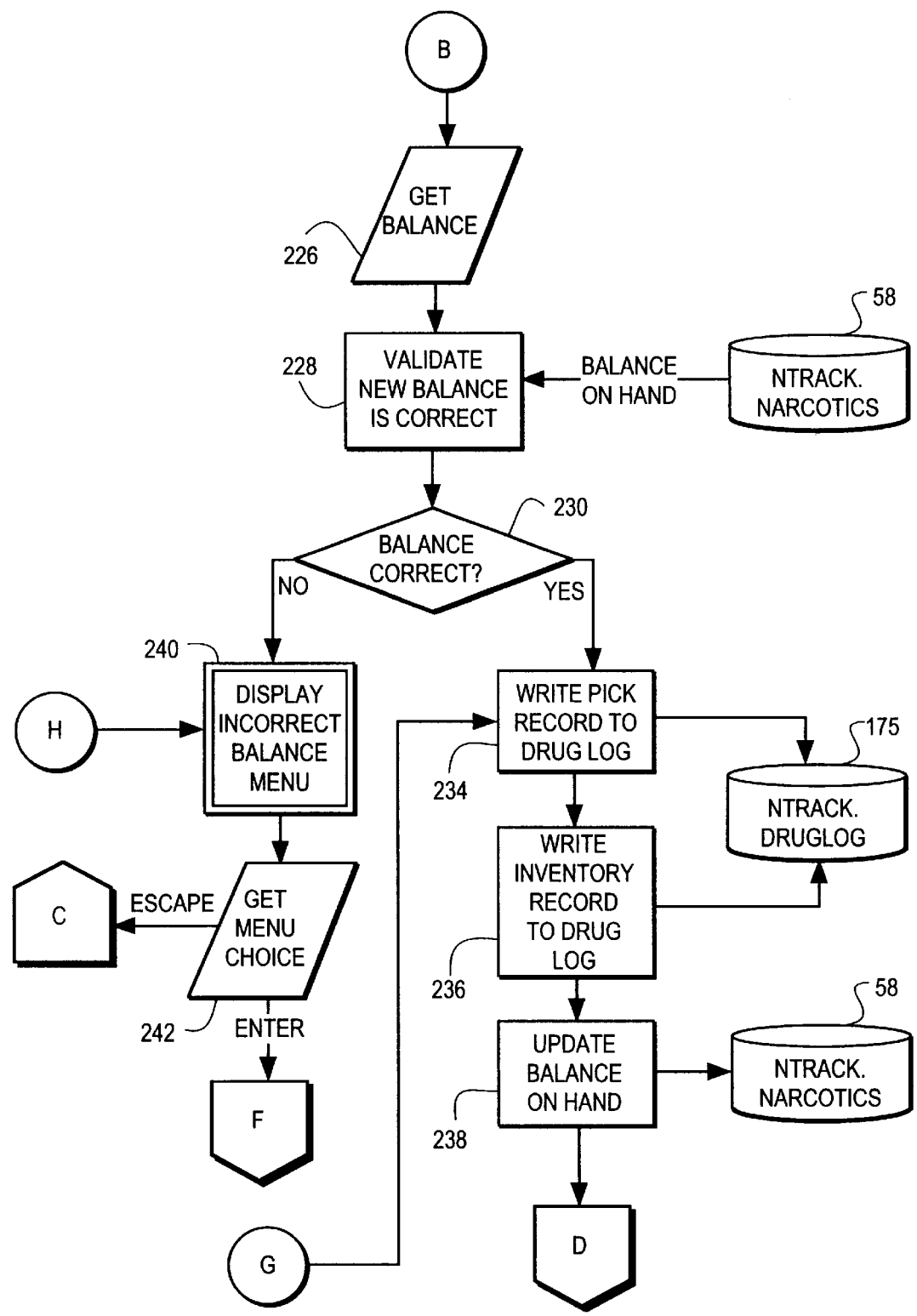
Figure 9D:
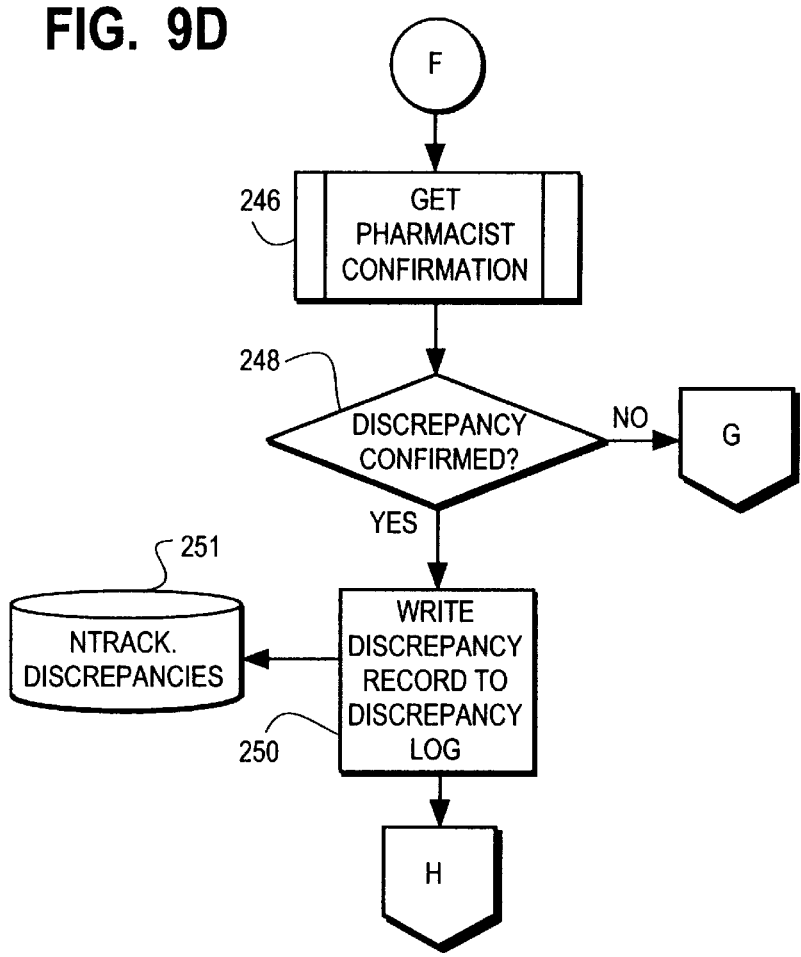
Figure 9E:
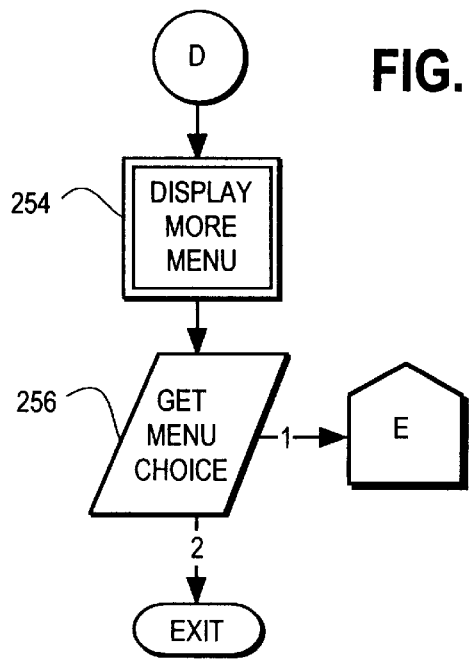
Figure 10A:
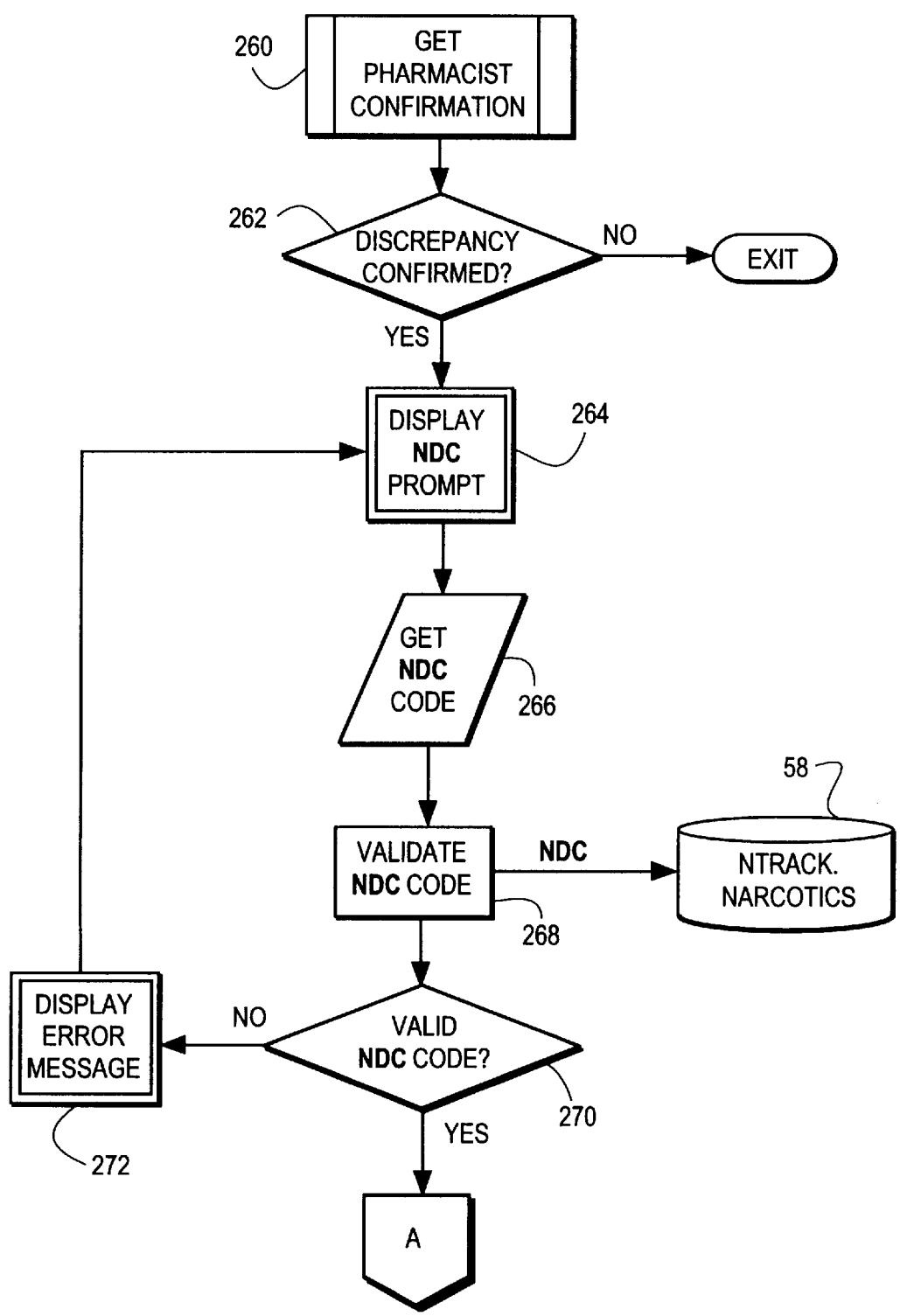
FIGS. 10, 10B, 10C and 10D illustrate an operation of the portable scanning and printing system for performing an outdating operation for inventoried drugs.
Figure 10B:
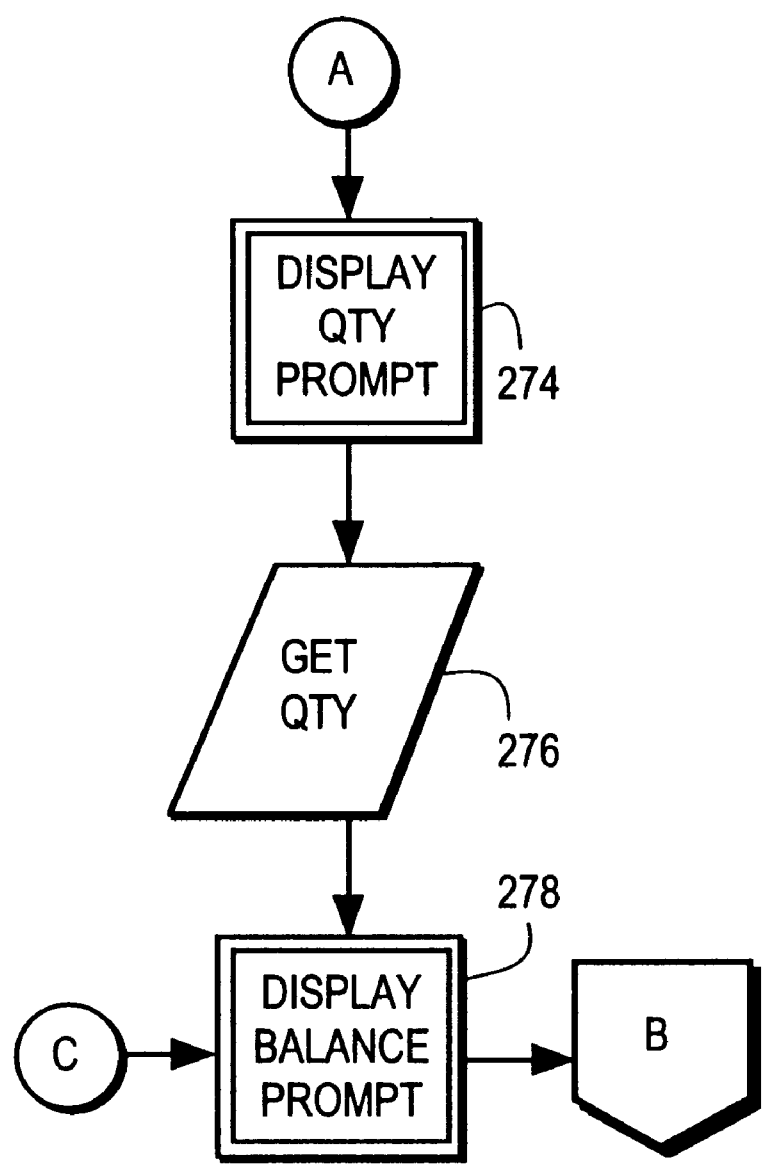
Figure 10C:
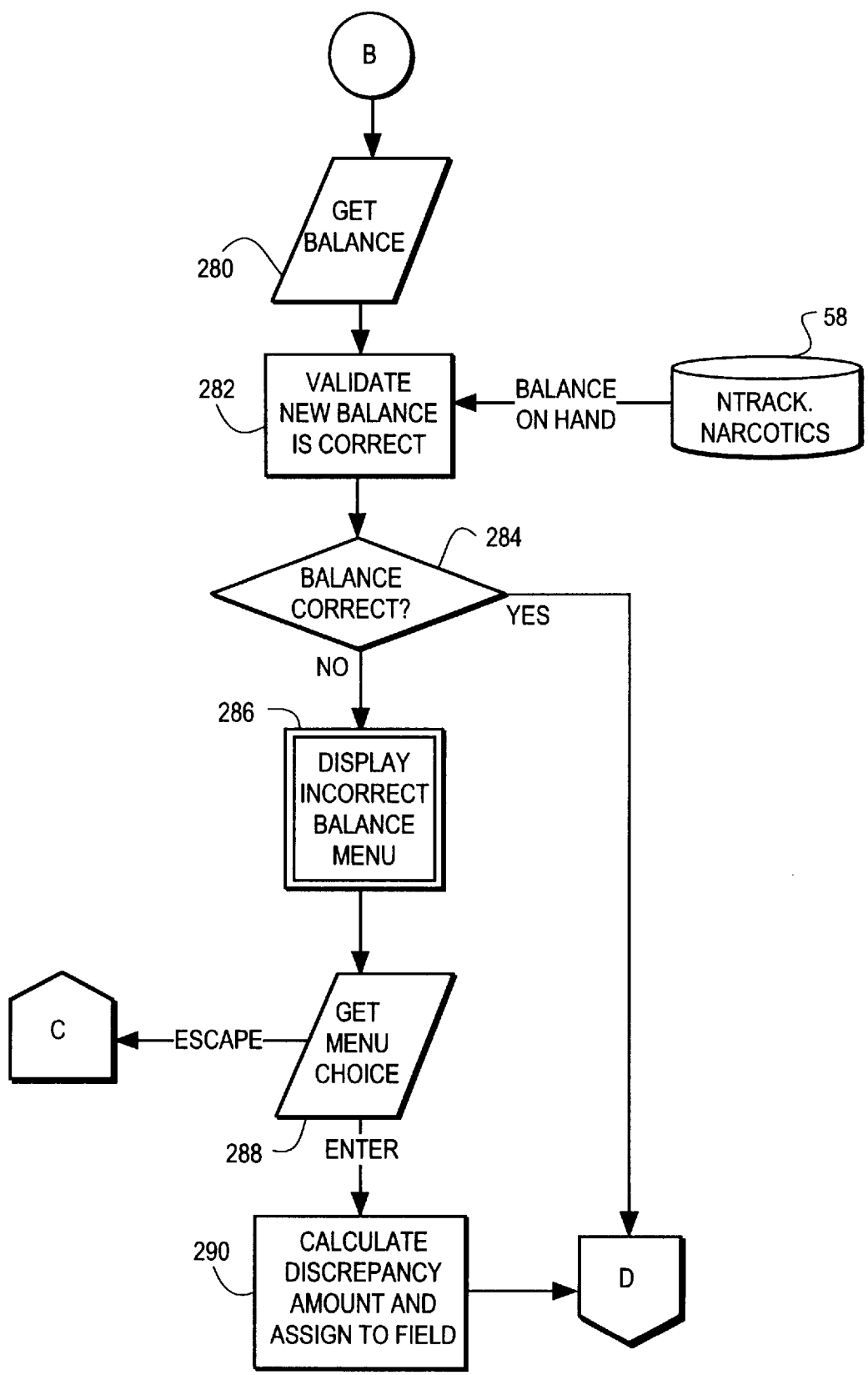
Figure 10D:
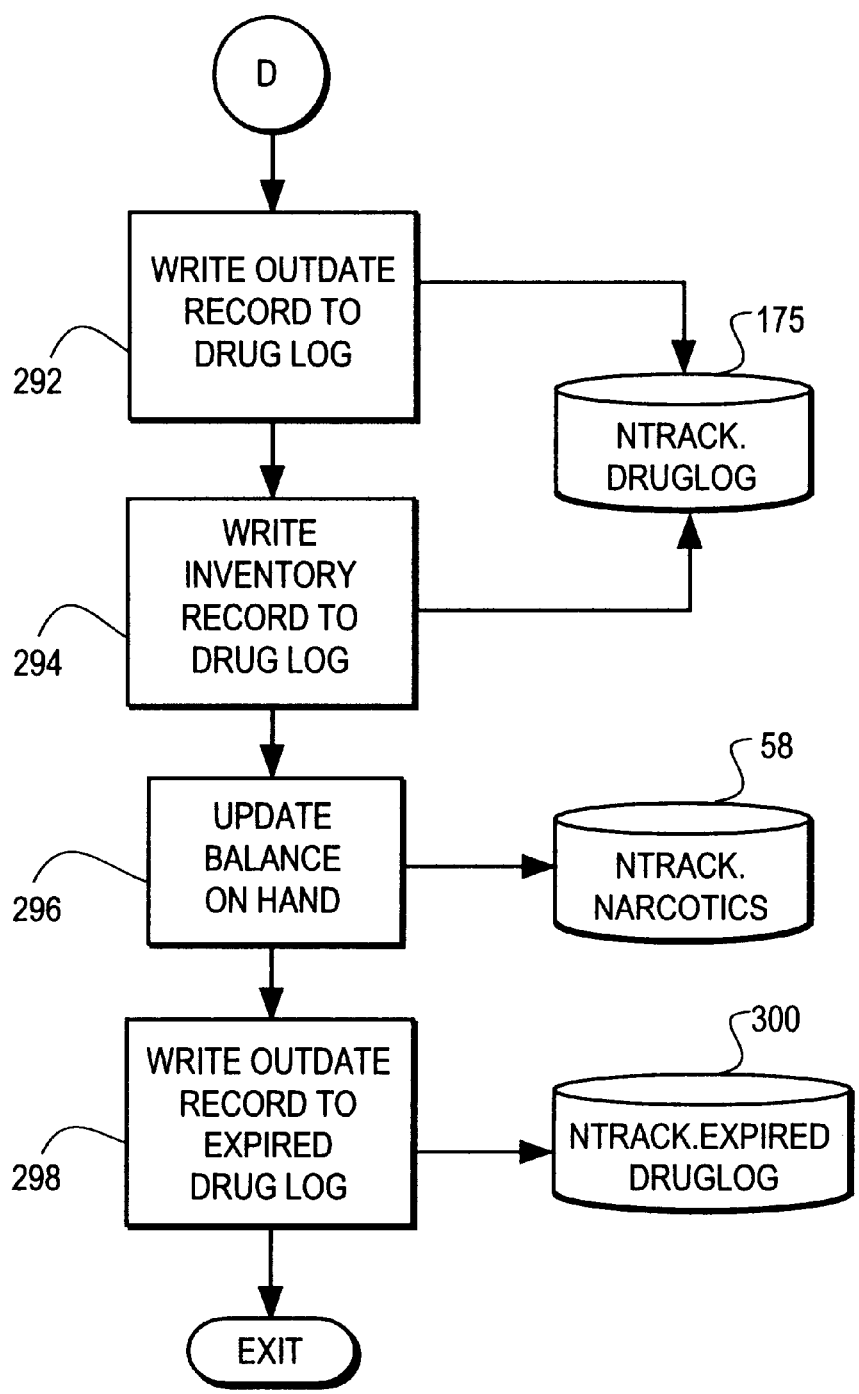

As shown in FIG. 8, the processing unit 32 obtains the pharmacist's user identification at block 184 from one of the input means as discussed above with respect to the user identification. Thereafter, the processing unit receives at block 186 from the keyboard an authorization code entered by the physician. At block 188, the portable scanning and printing system requests information from the host system 10 so as to confirm at block 192 that the correct and valid data was received at block 184 and 186. If the data was not correct, the system 20 will allow the pharmacist to re-enter the information by returning to block 184. Thereafter, the processing unit returns to the routine depicted in FIG. 7D so as to determine at block 194 whether the discrepancy noted in the balance keyed in by the user and the system's records has been confirmed by an authorized pharmacist. If the discrepancy was not confirmed, the processing unit will cause the display 28 to depict the incorrect balance menu at block 178. If however, the pharmacist confirms the discrepancy, the processing unit 32 will proceed to block 196 to set a discrepancy variable equal to the amount of the discrepancy i.e., the difference between the user entered balance representing the counted quantity of the drug remaining at the location and the balance on hand contained in the records of the data system 10. From block 196, the processing unit returns to block 172 to create the necessary records for the drug at blocks 172, 174 and 176 and to transmit the updated records including the discrepancy record to the host system 10 for updating the host's records for the drug.

Because the portable barcode scanning and printing system automatically prompts the user to pick a particular drug for a particular station by displaying the identity of the drug and the station identity as well at block 114, the user is lead through the picking operation very easily so as to improve accuracy of the picking and the drug tracking. Further, because the portable scanning and printing system is collecting the information entered by the user, such as the scanned drug identity data and keyboard entered quantity data, and is associating the data received from the different input means in the memory 34 with a particular pick-list record and drug or narcotics record received from the host, the system 20 can select portions of the associated data for printing labels and/or reports via the barcode printer 30. The system 20 can also automatically create and/or update different drug tracking records. By thereafter transmitting the updated records to the host system for storage, the record keeping operation is automatically accomplished and greatly simplified so as to improve the accuracy of the drug tracking operation.

FIGS. 9A–9E illustrates a software routine executed by the portable scanning and printing system 20 to allow drugs to be picked and inventoried without receipt of a picking list from the host system and to allow drugs to be received, i.e. added to the location so as to provide a drug tracking receiving operation. The routine depicted in FIGS. 9A–E can be entered from the picking routine 91 if the No Pick-List Picking operation is selected or it may be entered from the Receiving routine 92 as shown in FIG. 4. Upon entering the routine of FIGS. 9A–E, the processing unit 32 at block 200 displays a prompt for the station i.e. the intended destination for the drug if in the No Pick List Picking mode or the source of the drug if in the Receiving mode. It is noted, that in the Receiving mode, the source of the drug can either be a wholesaler identification or, for example, a nursing station that is returning a drug. Upon receiving a station identification at block 202 from either the scanner 22 or keyboard 24, the processing unit 32 at block 204 validates the station by communicating with the host system 10 utilizing the station records 42 of the host's memory. Thereafter, if the processing unit determines at block 206 that the station information received at block 202 is valid, the processing unit proceeds to block 208. Otherwise, the processing unit returns to block 200 to prompt the user to re-enter the station identification. At block 208, the processing unit controls the display 28 to prompt the user to enter NDC data for the drug being picked or received from the barcode scanner 22, the processing unit proceeds to block 214 to validate the scanned NDC code received at block 210 by communicating with the host system 10 using the narcotics records 58 of the host system's memory. The validation by the portable scanning and printing system 20 can be accomplished by the processing unit 32 comparing NDC information received from the host's narcotics records 58 to the user entered NDC information to determine if there is a match. Alternatively, the validation by the portable scanning and printing system 20 can be accomplished by the processing unit 32 transmitting the user entered NDC data to the host system and the P.C. 12 comparing the user entered NDC data with the NDC data contained in the host's narcotics records 58. The host then transmits the result of the comparison to the portable scanning and printing system 20. Based on the information received from the host system, the processing unit 32 determines at block 216 whether the scanned or keyboard entered NDC code is valid. If it is not valid, the processing unit 32 controls the display 28 to display an error message at block 218 and returns to block 208 to again prompt for the entry of the NDC information. If the user entered NDC code is determined to be valid at block 216, the processing unit 32 proceeds to block 220.

The processing unit 32 at block 220 controls the display 28 to display a message to prompt the user to enter the quantity to be picked or the quantity to be received depending on the mode. At block 222, the processing unit 32 receives the quantity data from the keyboard 24 and thereafter displays at block 224 a prompt for the user to enter the balance remaining after the quantity of the drug entered at block 222 has been removed from the location for picking or added to the location for receiving. At block 226, the processing unit 32 receives the balance data keyed in by the user and at block 228, the processing unit 32 validates the user entered balance by communicating with the host system 10 using the balance on hand information contained in the Narcotics record 58 of the host system's memory. As discussed above, this validation at block 228 may be implemented by the portable scanning and printing system 20 by the processing unit 32 comparing the user entered balance with the balance on hand information transmitted from the host system 10 or by the host system comparing the user entered balance as transmitted by the system 20 with the balance on hand data stored in the narcotics records 58 in which case the host transmits a message back to the portable scanning and printing system 20 with the results of the match. From block 228, the processing unit proceeds to block 230 to determine whether the user entered balance is correct for validation. If the user entered balance is validated at block 230, the processing unit proceeds to block 234 to write a Pick record from data stored in the memory 34 in association with the station entered at block 202, the NDC entered at block 210, the quantity entered at block 22 and the balance entered at 226. This Pick record is stored in the memory 34 and block 234 and transmitted to the host system so as to update the Drug Log 175 in the host's memory. The processing unit 32 also stores an inventory record in the memory 34 at block 236 and transmits the inventory record to the host processing system for updating the Drug Log 175 in the host's memory. At block 238, the balance on hand for the drug is updated in the memory 34 and transmitted to the host system 10 for updating the host's Narcotics records 58. From block 238, the processing unit proceeds to block 254 shown in FIG. 11E so as to display a menu to allow the user to pick or receive more drugs by returning to block 200 or to allow the user to exit the routine.

If the processing unit 32 does not validate the user entered balance at block 230, the processing unit proceeds to block 240. At block 240, the processing unit displays an Incorrect Balance Menu on the display 28 and proceeds to block 242 to obtain the user's menu selection. One option depicted on the Incorrect Balance Menu at block 240 is to obtain pharmacist confirmation of a discrepancy which will be selected if the user determines that he has correctly counted and correctly entered the values prompted for at block 220 and 224. If this menu choice is selected by the user, the processing unit 32 proceeds from block 242 to block 246. At block 246, the processing unit executes the routine depicted in FIG. 8 and thereafter proceeds to block 248 to determine whether the discrepancy has been confirmed by an authorized physician as discussed above. If the discrepancy was not confirmed, the processing unit proceeds from block 248 to block 234 and if the discrepancy was confirmed, the processing unit proceeds to block 250. At block 250, the processing unit writes a Discrepancy record in the memory 34 and transmits the Discrepancy record to the host system 10 so as to update the host's Discrepancy Log 251.

If the user selects an outdates operation from the menu 88 depicted in FIG. 4, the outdates routine 93 allows the user to select either an outdate safe inventory routine or an outdate received narcotics routine. The outdate safe inventory routine allows drugs that are stored in the safe and inventoried therein to be outdated by removing the drugs from their current location within the safe to an outdate area for destruction. The outdate received narcotics routine allows drugs received from a nurse's station to be outdated without performing an inventory.

The outdate safe inventory routine is depicted in FIGS. 10A–10D. In this routine, the processing unit 32 first obtains pharmacist confirmation at block 260 by executing the routine depicted in FIG. 8 since a pharmacist is required to handle the outdate procedure. If a pharmacist is not confirmed by the processing unit as determined at block 262, the processing unit exits the routine. However, if confirmation is obtained at block 262, the processing unit 32 proceeds to block 264 to display a message prompting the user to enter NDC data for the drug to be outdated. Upon receiving the NDC data from either the barcode scanner 22 or the keyboard 24 at block 266, the processing unit 32 proceeds to block 268 to validate the user entered NDC data by communicating with the host system using the narcotics records 58 of the host as discussed above. If the processing unit 32 determines at block 270 that the user entered NDC information is not valid, the processing unit controls the display to depict a message to that effect at block 272 and returns back to block 264 to again prompt the user to enter the NDC information. If the processing unit 32 determines that a valid NDC code has been entered by the user, the processing unit proceeds from block 270 to block 274 to display a message to the user to prompt the user to enter the quantity of the drug to be outdated from the safe's inventory. The processing unit at block 276 receives the user entered quantity from the keyboard 24. At block 278 the processing unit controls the display 28 to depict a message prompting the user to enter the quantity of the drug remaining after the quantity of the drug entered at block 276 has been removed from the location for outdating.

The processing unit 32 receives this user enteredbalance information from the keyboard 24 at block 280. Thereafter, the processing unit 32 at block 282 validates the user entered balance by communicating with the host system using the narcotics records 58 of the host as discussed above. At block 284, the processing unit 32 determines whether the balance is valid, i.e., whether it matches the balance on hand maintained in the host's narcotics records and if so, the processing unit proceeds to block 292. If the user entered balance is determined to be invalid at block 284, the processing unit proceeds to block 286 to display an Incorrect Balance Menu on the display 28 and thereafter receives the user's selection at block 288. The Incorrect Balance Menu allows the user to acknowledge the discrepancy. If the discrepancy is acknowledged, the processing unit proceeds to block 290 to calculate a discrepancy amount, i.e. the difference between the user entered balance and the balance on hand from the host's narcotics records 58 and to assign this calculated value to a discrepancy field. At block 292, the processing unit updates the outdate record in the memory 34 and transmits the outdate record to the host to update the host's Drug Log 175. At block 294, the processing unit updates the inventory record in the memory 34 and transmits the inventory record to the host system to update the drug logs 175 with the information contained therein. The host processing system also updates the balance on hand in the memory 34 at block 296 and transmits this information to the host system for updating the host's narcotics records 58. Thereafter, an outdate record is updated in the memory 34 at block 298 and transmitted to the host 10 so as to update the expired drug log 300 maintained in the host's memory.

Figure 11A:
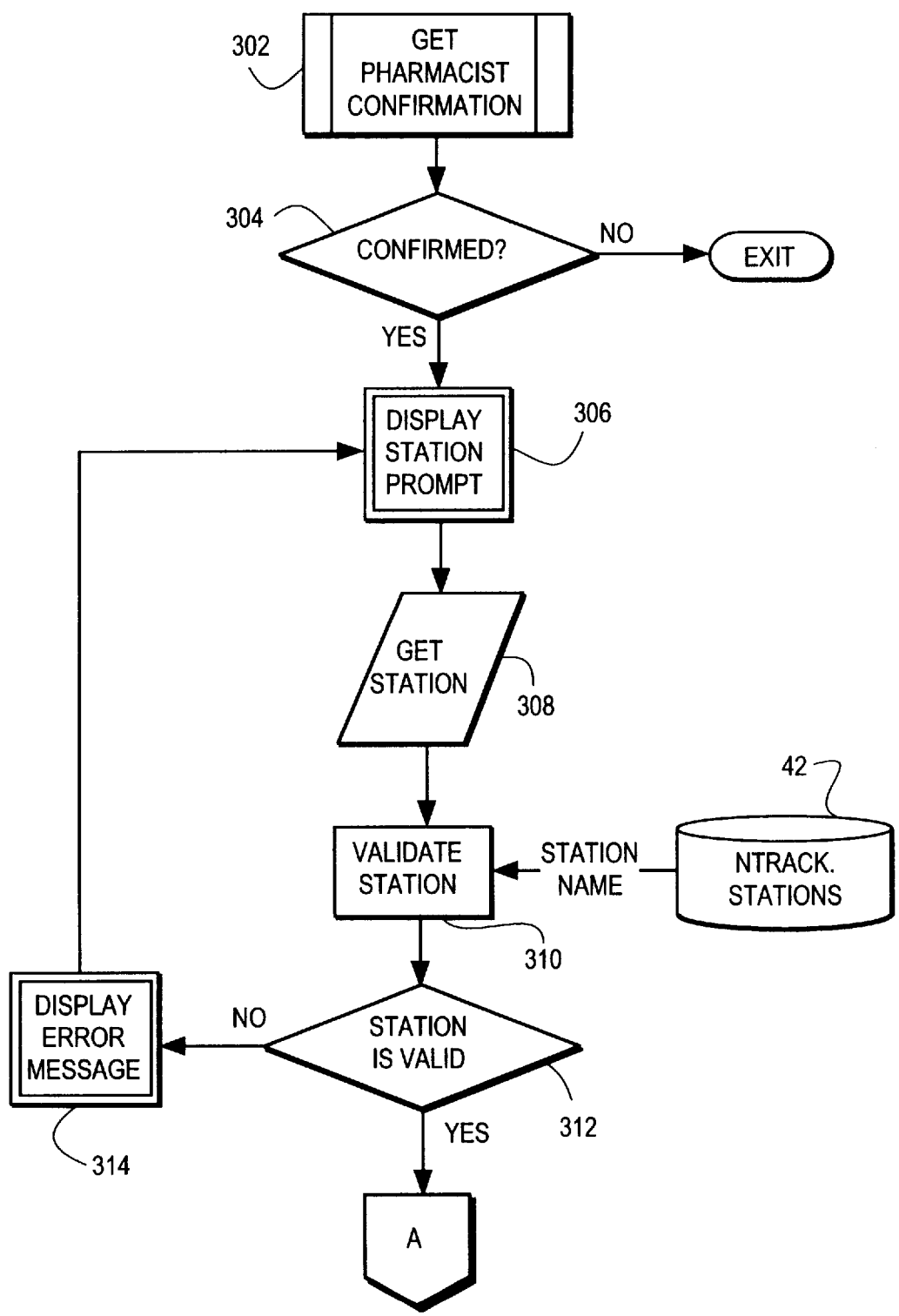
FIGS. 11A and 11B form a flow chart illustrating an operation of the portable scanning and printing system for outdating drugs that are not inventoried.
Figure 11B:
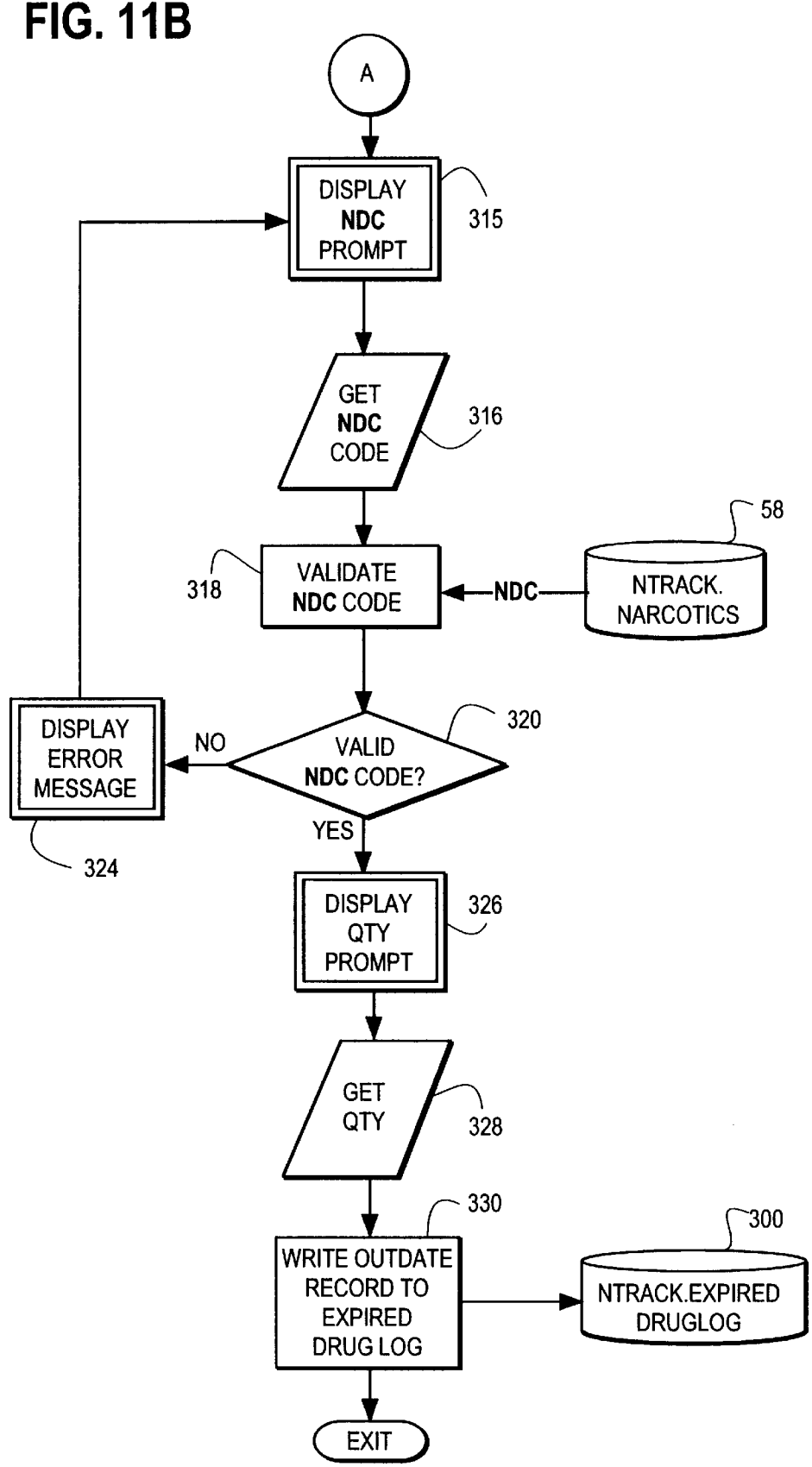

The Outdate Received Narcotics routine is depicted in FIGS. 11A–11B. Upon entering this routine, the processing unit at block 302 executes the pharmacist's confirmation routine depicted in FIG. 8. Upon obtaining information that an authorized pharmacist is performing the outdate procedure as determined by the processing unit at block 304, the processing unit 32 proceeds to block 306 to display a message on the display 28 to prompt the user to enter the station, i.e. the source, of the drug to be outdated. At block 308, the processing unit receives the station information entered by the user via the input means and proceeds to block 310. At block 310 the processing unit 32 validates the user entered station by communicating with the host system 10 using the host's station records 42. At block 312, the processing unit determines whether the user entered station is valid and if not, controls the display 28 to depict an error message 314. From block 314, the processing unit returns to block 306. If the user entered station is determined to be valid at block 312, the processing unit proceeds to block 315 to control the display 28 to depict a message prompting the user to enter NDC data for the drug to be outdated from the identified station. At block 316, the processing unit receives the user entered NDC data and at block 318 validates the user entered data by communicating with the host system using the host's narcotics records 58. At block 320, the processing unit determines whether the user entered NDC information is valid and if not the processing unit controls the display 28 at block 324 to display an error message and the processing unit returns to block 315. If the processing unit determines at block 320 that the user entered NDC information is valid, the processing unit at block 326 controls the display 328 to depict a message to prompt the user to enter the quantity of the drug to be outdated. Thereafter, at block 328, the processing unit receives the user entered quantity. At block 330 the processing unit updates an outdate record in the memory 34 and transmits the outdate record to the host system 10 to update the Expired Drug Log record 300 in the host's memory.

Figure 12A:
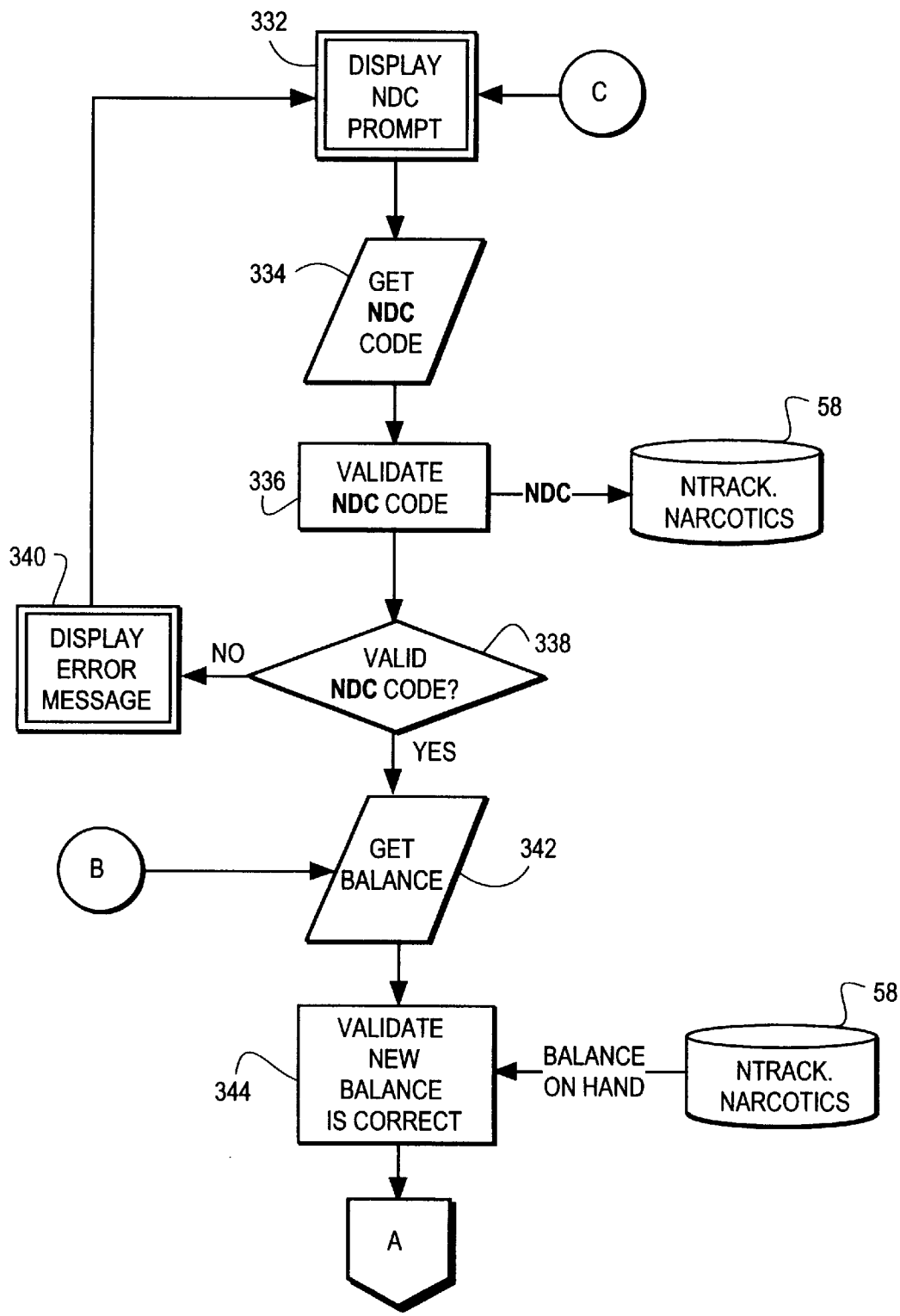
FIGS. 12A, 12B and 12C form a flow chart illustrating an operation of the portable scanning and printing system for providing an inventory of drugs maintained at a location.
Figure 12B:
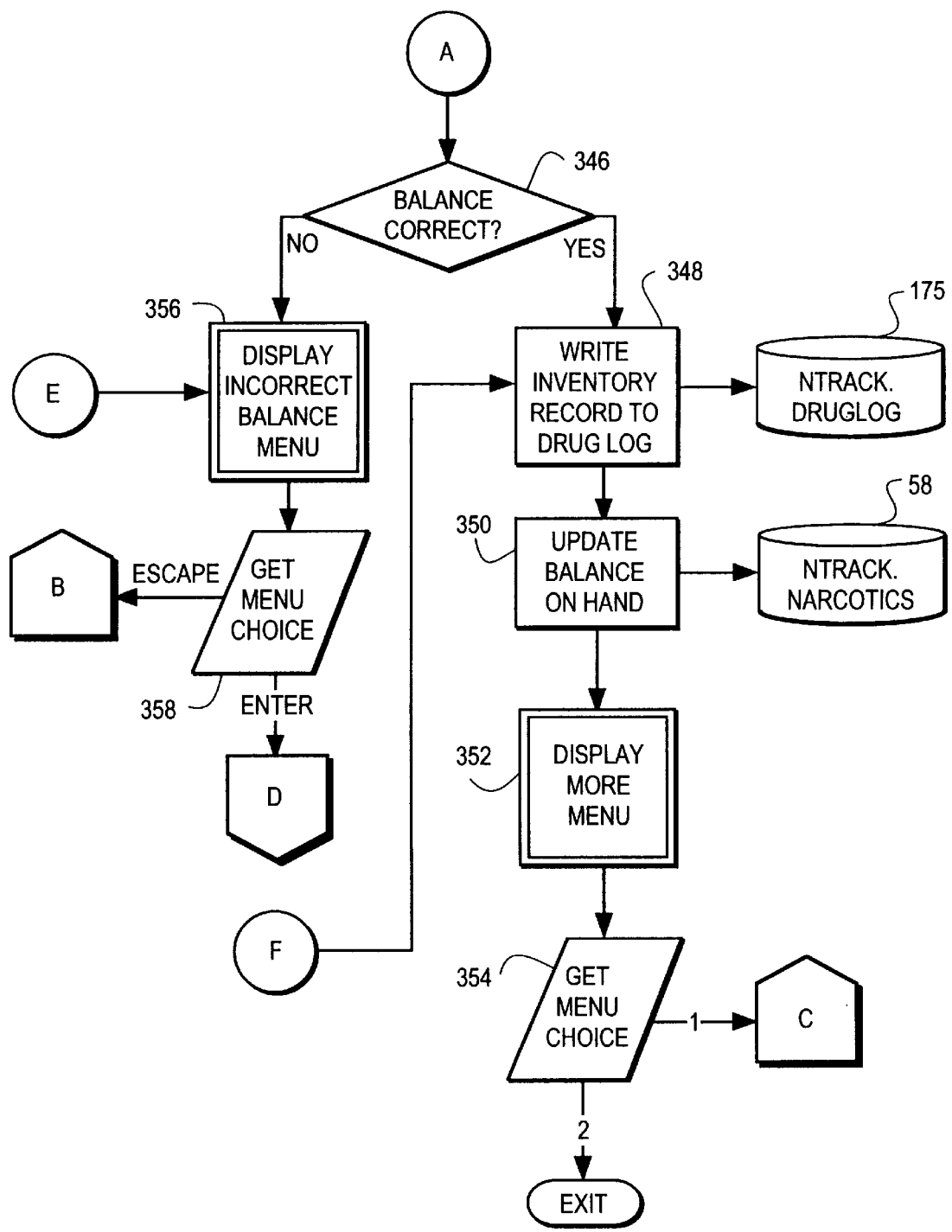
Figure 12C:
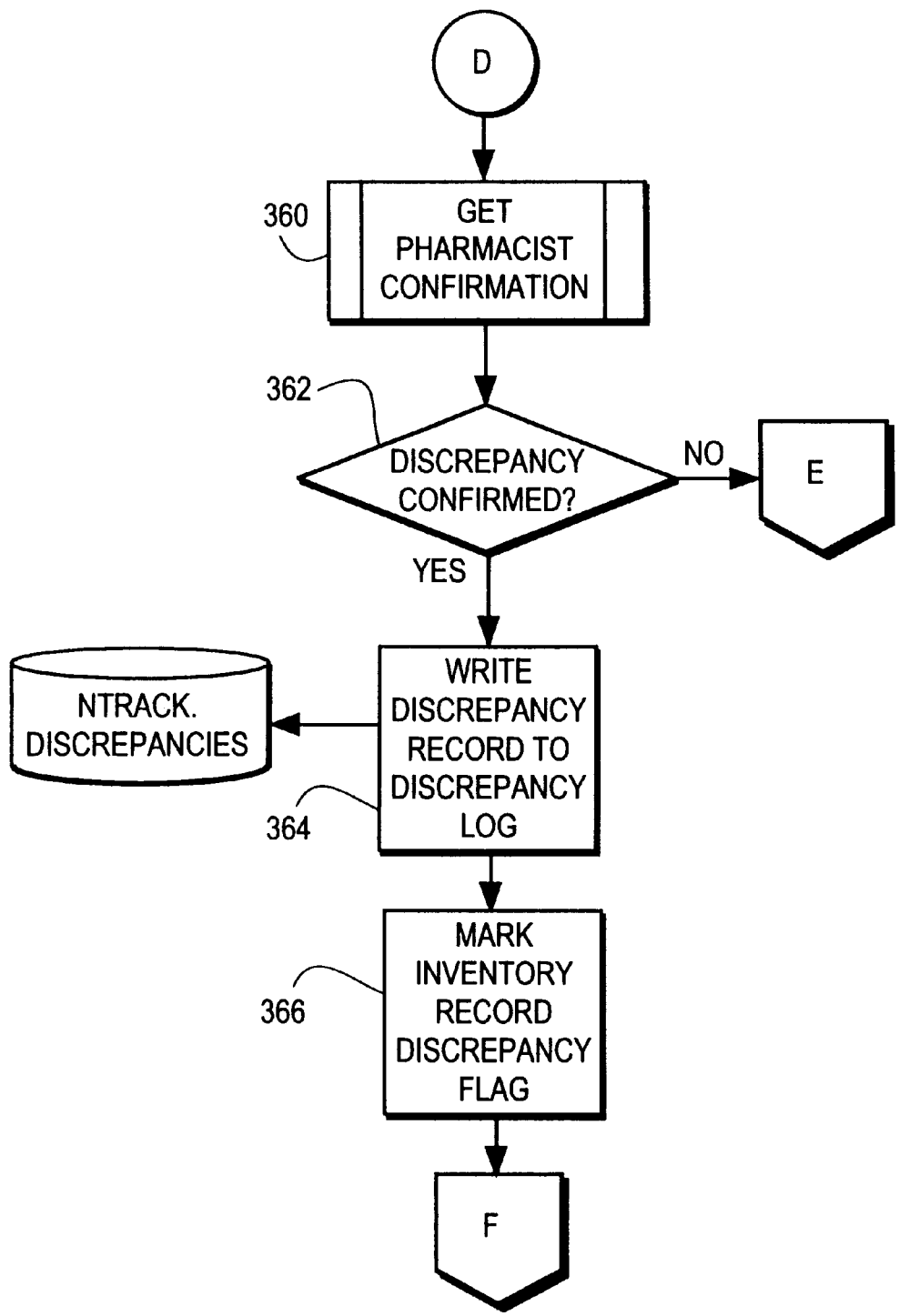

If a user selects the inventory operation from the main menu displayed at block 88, at block 94 of FIG. 4, the processing unit 32 executes the routine depicted in FIGS. 12A–12C. This routine allows an inventory operation to be performed independent of picking, receiving and outdating. Upon entering the inventory routine at block 332, the processing unit 32 controls the display 28 to depict a message to prompt the user to enter NDC information. At block 334 the processing unit receives the entered NDC information from the input means used. The processing unit 32 then validates at block 336 the user entered NDC data by communicating with the host system 10 using the host's narcotics records 58. If the processing unit 32 determines at block 338 that the user entered NDC information is not valid in that it does not match a NDC code contained within the host's narcotics records 58, the processing unit proceeds to block 340 to control the display 28 to depict an error message. Thereafter, the processing unit proceeds to block 332 from block 340. If the user entered NDC data is determined to be valid at block 338 the processing unit at block 342 prompts the user to enter a balance value representing a quantity of the drug currently maintained at the location. At block 342, the processing unit receives the user entered balance data and proceeds to block 344. At block 344, the processing unit 32 validates the user entered balance by communicating with the host system 10 using the host's systems narcotics records 58. At block 346, the processing unit determines whether the user entered balance is valid and if so, the processing unit proceeds to block 348. At block 348, the processing unit updates an inventory record in the memory 34 and transmits the inventory record to the host system 10 so as to update the Drug Log 175 of the host's memory. At block 350, the processing unit updates the balance on hand data in the memory 34 and transmits the balance on hand information to the host system 10 so as to update the host's narcotics records 58. Thereafter, the processing unit proceeds to block 352 to display a menu to the user which allows the user to select an option to exit the routine or to select an option to inventory another drug maintained at the location. If the latter option is selected by the user, the processing unit proceeds from block 354 to block 332 to prompt the user to enter the NDC information associated with the next drug to be inventoried.

If the processing unit 32 determines at block 346 that the user entered balance is not valid, the processing unit proceeds from block 346 to block 356. At block 356, the processing unit controls the display 28 to depict an Incorrect Balance Menu. This menu allows the user to obtain pharmacist confirmation of a discrepancy. The processing unit proceeds from block 358 to block 360. At block 360, the processing unit obtains pharmacist confirmation by executing the routine depicted in FIG. 8. At block 362, the processing unit determines whether a pharmacist has confirmed the discrepancy and if not, the processing unit returns to block 356. If the discrepancy is confirmed as determined at block 362, the processing unit proceeds to block 364. At block 364 the processing unit updates a discrepancy record in the memory 34 and transmits the discrepancy record to the host system 10 via the communication interface 26 to update the Discrepancy Log maintained at the host system. Thereafter, at block 364, the processing unit marks an inventory record discrepancy flag associated with the inventoried drug in the memory 34 and proceeds from block 366 to block 348.

Many modifications and variations of the present invention are possible in light of the above teachings. For example, the drug tracking method of the present invention can be used at locations other than a drug safe including the nursing stations and any other source and/or destination of a drug. Further as noted above, the processing unit 32 may include one or more microprocessors. If multiple microprocessors or the like are employed, the above-described operations could be performed by any one or combination of the processors. For example, one processor could control scanning operations, another processor could control data collection operations and another processor might control printing operations as will be readily apparent to one of ordinary skill in the art. Because validation of user entered data, whether via the scanner 22 or keyboard 24, is performed automatically and non-validation results in a displayed prompt to the user to correct or confirm a discrepancy before proceeding, the user is forced to deal with the discrepancy immediately, when counting errors and data entry errors are most easily corrected. Thus, the system and method of the present invention increases the accuracy of the drug tracking operation. Thus, it is to be understood that, within the scope of the appended claims, the invention may be practiced otherwise than as described hereinabove.

What is claimed and desired to be secured by Letters Patent is:

1. A method of operating a portable scanning and printing system for tracking drugs maintained at a location, the portable scanning and printing system having a memory for collecting data, a display, a barcode printer and a plurality of input means including a barcode scanner, a keyboard and a wireless communication interface to allow wireless communication with a host system having a memory for storing drug tracking records, comprising:

receiving user identification information from one of the input means;

receiving from the scanner scanned barcode data representing the identity of a drug maintained at the location;

receiving from the keyboard data confirming a quantity of the drug being removed or added;

associating in the portable scanning and printing system memory, data received from a plurality of the input means for a drug;

transmitting to the host system via the communication interface information regarding the removal of the drug from the location or the addition of the drug to the location, including the user's identification, the identity of the drug and the quantity of the drug being removed or added;

receiving from the keyboard user entered balance data representing a quantity of the drug remaining at the location after the removal or addition of a quantity of the drug;

validating the user entered balance; and prompting the user via the display to select a displayed option for dealing with a discrepancy if the user entered balance is not validated including an option to obtain confirmation of a discrepancy by an authorized person.

2. A method of operating a portable scanning and printing system for tracking drugs as recited in claim 1 wherein said step of validating includes comparing a stored balance for the identified drug to the user entered balance to determine whether there is a match.

3. A method of operating a portable scanning and printing system for tracking drugs as recited in claim 2 including the step of receiving data from the host system via the wireless communication interface representing a balance for the drug and storing the received balance in association with the drug identity.

4. A method of operating a portable scanning and printing system for tracking drugs as recited in claim 3 including the step of automatically updating the stored balance by subtracting a confirmed quantity of a drug being removed from the stored balance to provide a new balance that is stored or by adding a confirmed quantity of a drug being added to the stored balance to provide a new balance that is stored.

5. A method of operating a portable scanning and printing system for tracking drugs as recited in claim 1 including the step of transmitting a validated user entered balance to the host system.

6. A method of operating a portable scanning and printing system for tracking drugs as recited in claim 1 wherein the step of validating includes transmitting a user entered balance to the host system for comparison to a balance stored in the host system for the drug to determine whether there is a match and receiving from the host system a result of the host system's comparison.

7. A method of operating a portable scanning and printing system for tracking drugs as recited in claim 1 wherein the step of prompting the user to deal with the discrepancy includes displaying a message to the user with a selectable option to re-enter the user entered balance.

8. A method of operating a portable scanning and printing system for tracking drugs as recited in claim 1 wherein the step of prompting the user to deal with the discrepancy includes displaying a message to the user with a selectable option to re-enter the quantity of the drug being removed or added.

9. A method of operating a portable scanning and printing system for tracking drugs as recited in claim 1 including the step of generating a record of a discrepancy upon confirmation of the discrepancy by an authorized person; and transmitting a discrepancy record to the host upon confirmation.

10. A method of operating a portable scanning and printing system for tracking drugs as recited in claim 1 including the step of printing information on a label including a barcode identifying the drug being removed or added.

11. A method of operating a portable scanning and printing system for tracking drugs as recited in claim 10 including the step of receiving information identifying a source of a drug being added or a destination of a drug being removed and wherein the step of printing includes printing information including the source or destination of a drug.

12. A method of operating a portable scanning and printing system for tracking drugs as recited in claim 1 including the steps of receiving from the host system via the communication interface information identifying a drug to be removed from the location, a quantity of the drug to be removed and an intended destination;

displaying information to the user to prompt the user to select a drug identified by information received from the host system;

receiving from the scanner scanned barcode data representing the identity of a drug maintained at the location;

comparing the identity of the drug represented by the scanned barcode data to the identity of the drug received from the host system; and displaying an error message to the user if the identity of the drug represented by the scanned barcode does not match the identity of the drug received from the host system.

13. A method of operating a portable scanning and printing system for tracking drugs maintained at a location, the portable scanning and printing system having a memory for collecting data, a display, a barcode printer and a plurality of input means including a barcode scanner, a keypad and a wireless communication interface to allow wireless communication with a host system having a memory for storing drug tracking records, comprising:

displaying a message to a user on the display to prompt the user to enter an identity of a drug maintained at the location;

receiving user entered drug identity data;

displaying a message to a user on the display to prompt the user to enter a quantity of the drug to be added to or removed from the locations;

receiving user entered data representing the quantity of the drug being added to or removed from the location;

displaying a message to a user on the display to prompt the user to enter a balance representing the quantity of the drug being maintained at the location after the addition or removal of the drug;

validating the user entered balance; and prompting the user via the display to select a displayed option from dealing with a discrepancy if the user entered balance is not valid including an option to obtain confirmation of a discrepancy by an authorized person.

14. A method of operating a portable scanning and printing system for tracking drugs as recited in claim 13 including the step of transmitting to the host system via the wireless communication interface selected data received from said input means in association with the entered identity of the drug.

15. A method of operating a portable scanning and printing system for tracking drugs as recited in claim 13 wherein said step of validating includes comparing a stored balance for the identified drug to the user entered balance to determine whether there is a match.

16. A method of operating a portable scanning and printing system for tracking drugs as recited in claim 15 including the step of receiving data from the host system via the wireless communication interface representing a balance for the drug and storing the received balance in association with the drug identity.

17. A method of operating a portable scanning and printing system for tracking drugs as recited in claim 16 including the step of automatically updating the stored balance by subtracting a confirmed quantity of a drug being removed from the stored balance to provide a new balance that is stored or by adding a confirmed quantity of a drug being added to the stored balance to provide a new balance that is stored.

18. A method of operating a portable scanning and printing system for tracking drugs as recited in claim 13 including the step of transmitting a validated user entered balance to the host system.

19. A method of operating a portable scanning and printing system for tracking drugs as recited in claim 13 wherein the step of validating includes transmitting a user entered balance to the host system for comparison to a balance stored in the host system for the drug to determine whether there is a match and receiving from the host system a result of the host system's comparison.

20. A method of operating a portable scanning and printing system for tracking drugs as recited in claim 13 wherein the step of prompting the user to deal with the discrepancy includes displaying a message to the user to obtain a pharmacist's confirmation.

21. A method of operating a portable scanning and printing system for tracking drugs as recited in claim 13 wherein the step of prompting the user to deal with the discrepancy includes displaying a message to the user to prompt re-enter of information.

22. A method of operating a portable scanning and printing system for tracking drugs as recited in claim 13 wherein the step of prompting the user to deal with the discrepancy includes displaying a message to the user with a selectable option to obtain confirmation of the discrepancy by an authorized person.

23. A method of operating a portable scanning and printing system for tracking drugs as recited in claim 13 including the step of printing information on a label including a barcode identifying the drug being removed or added.

24. A method of operating a portable scanning and printing system for tracking drugs as recited in claim 23 including the step of receiving information identifying a source of a drug being added or a destination of a drug being removed and wherein the step of printing includes printing information including the source or destination of a drug.

25. A method of operating a portable scanning and printing system for tracking drugs as recited in claim 13 including the steps of
   receiving from the host system via the communication interface information identifying a drug to be removed from the location, a quantity of the drug to be removed and an intended destination;
   displaying information to the user to prompt the user to select a drug identified by information received from the host system;
   receiving from the scanner scanned barcode data representing the identity of a drug maintained at the location;
   comparing the identity of the drug represented by the scanned barcode data to the identity of the drug received from the host system; and
   displaying an error message to the user if the identity of the drug represented by the scanned barcode does not match the identity of the drug received from the host system.

26. A method of operating a portable scanning and printing system for tracking drugs maintained at a location, the portable scanning and printing system having a memory for collecting data, a display, a barcode printer and a plurality of input means including a barcode scanner, a keypad and a wireless communication interface to allow wireless communication with a host system having a memory for storing drug tracking records comprising:
   receiving from the host system via the communication interface information identifying a drug to be removed from the location, a quantity of the drug to be removed and an is intended destination;
   displaying information to the user to prompt the user to select a drug identified by information received from the host system;
   receiving from the scanner scanned barcode data representing the identity of a drug maintained at the location;
   comparing the identity of the drug represented by the scanned barcode data to the identity of the drug received from the host system; and
   displaying an error message to the user if the identity of the drug represented by the scanned barcode does not match the identity of the drug received from the host system.

27. A method of operating a portable scanning and printing system for tracking drugs maintained at a location as recited in claim 26 including the step of printing information on at least one label for the drug being removed, the printed information including the identity of the drug and the intended destination.

28. A method of operating a portable scanning and printing system for tracking drugs maintained at a location as recited in claim 26 including the steps of
   receiving user identification information from one of the input means;
   receiving information from the keyboard confirming a quantity of the drug being removed; and
   transmitting to the host station via the communication interface information regarding the removal of the drug from the location including the user's identification, the identity of the drug and the quantity of the drug being removed.

29. A method of operating a portable scanning and printing system for tracking drugs maintained at a location as recited in claim 28 including the steps of
   receiving from the keyboard user entered balance data representing a quantity of the- drug remaining at the location;
   receiving from the host system via the communication interface data representing a balance of the drug stored in the host system's drug tracking records; and
   validating the user entered balance data with information received from the host.

30. A method of operating a portable scanning and printing system for tracking drugs as recited in claim 29 wherein the validating step includes comparing the balance data received from the host with the user entered balance data.

31. A method of operating a portable scanning and printing system for tracking drugs as recited in claim 29 wherein the validating step includes updating the balance data received from the host to account for a received confirmed quantity of the drug being removed; and comparing the balance data received from the host with the user entered balance data.

32. A method of operating a portable scanning and printing system for tracking drugs maintained at a location, the portable scanning and printing system having a memory for collecting data, a display, a barcode printer and a plurality of input means including a barcode scanner, a keypad and a wireless communication interface to allow wireless communication with a host system having a memory for storing drug tracking records comprising:

receiving from the scanner scanned barcode data representing the identity of a drug maintained at the location;

receiving from the keyboard data confirming a quantity of the drug being added to the location or removed from the location;

transmitting to the host system via the communication interface information regarding a drug's addition to or removal from the location including the identity of the drug and the quantity of the drug being added to or removed from the location;

receiving from the keyboard user entered balance data confirming a quantity of the drug maintained at the location after the drugs addition to or removal from the location; and validating the user entered balance data by communicating with the host system; and prompting the user to obtain confirmation of a discrepancy if the user entered balance is not valid.

33. A method of operating a portable scanning and printing system for tracking drugs as recited in claim 32 wherein said step of validating includes comparing a stored balance for the identified drug to the user entered balance to determine whether there is a match.

34. A method of operating a portable scanning and printing system for tracking drugs as recited in claim 33 including the step of receiving data from the host system via the wireless communication interface representing a balance for the drug and storing the received balance in association with the drug identity.

35. A method of operating a portable scanning and printing system for tracking drugs as recited in claim 34 including the step of automatically updating the stored balance by subtracting a confirmed quantity of a drug being removed from the stored balance to provide a new balance that is stored or by adding a confirmed quantity of a drug being added to the stored balance to provide a new balance that is stored.

36. A method of operating a portable scanning and printing system for tracking drugs as recited in claim 32 including the step of transmitting a validated user entered balance to the host system.

37. A method of operating a portable scanning and printing system for tracking drugs as recited in claim 32 wherein the step of validating includes transmitting a user entered balance to the host system for comparison to a balance stored in the host system for the drug to determine whether there is a match and receiving from the host system a result of the host system's comparison.

38. A method of operating a portable scanning and printing system for tracking drugs as recited in claim 32 wherein the step of prompting the user to includes displaying a message to the user with a selectable option to re-enter the user entered balance.

39. A method of operating a portable scanning and printing system for tracking drugs as recited in claim 32 wherein the step of prompting the user to includes displaying a message to the user with a selectable option to re-enter the quantity of the drug being removed or added.

40. A method of operating a portable scanning and printing system for tracking drugs as recited in claim 32 including the step of generating a record of a discrepancy upon confirmation of the discrepancy by an authorized person; and transmitting a discrepancy record to the host upon confirmation.

41. A method of operating a portable scanning and printing system for tracking drugs as recited in claim 32 including the step of printing information on a label including a barcode identifying the drug being removed or added.

42. A method of operating a portable scanning and printing system for tracking drugs as recited in claim 32 including the step of receiving information identifying a source of a drug being added or a destination of a drug being removed and wherein the step of printing includes printing information including the source or destination of a drug.

43. A method of operating a portable scanning and printing system for tracking drugs maintained at a location, the portable scanning and printing system having a memory for collecting data, a display, a printer and a plurality of input means including a barcode scanner, a keyboard and a wireless communication interface to allow wireless communication with a host system having a memory for storing drug tracking records comprising:

receiving from the scanner scanned barcode data representing the identity of a drug maintained at the location;

transmitting to the host system data representing the identity of the drug received from the scanner;

receiving information from the host system representing the validity of the identity of the drug transmitted to the host;

receiving from the keyboard data representing a quantity of the drug maintained at the location;

receiving from the host system data representing the balance of the drug that the host's data tracking records indicate should be remaining at the location;

comparing the quantity of the drug maintained at the location as received from the keyboard and the balance received from the host to determine if they match; and displaying a selectable option to the user to allow a confirmation of a discrepancy by an authorized person if the comparison results in a no match determination.

\* \* \* \* \*